United States Patent
Tsutsui et al.

(10) Patent No.: US 10,450,583 B2
(45) Date of Patent: Oct. 22, 2019

(54) COMPOSITIONS AND METHODS FOR CONTROLLING PESTS

(71) Applicant: The Regents of the University of California, Oakland, CA (US)

(72) Inventors: Neil D. Tsutsui, Berkeley, CA (US); Maria Tonione, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/303,173

(22) PCT Filed: Apr. 22, 2015

(86) PCT No.: PCT/US2015/027147
§ 371 (c)(1),
(2) Date: Oct. 10, 2016

(87) PCT Pub. No.: WO2015/164529
PCT Pub. Date: Oct. 29, 2015

(65) Prior Publication Data
US 2017/0029846 A1    Feb. 2, 2017

Related U.S. Application Data

(60) Provisional application No. 61/983,364, filed on Apr. 23, 2014.

(51) Int. Cl.
*C12N 15/82* (2006.01)
*C12N 15/113* (2010.01)

(52) U.S. Cl.
CPC ...... *C12N 15/8286* (2013.01); *C12N 15/1137* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 2012/0137387 A1* | 5/2012 | Baum | C07H 21/04 800/279 |
| 2012/0240288 A1 | 9/2012 | Ye et al. | |
| 2012/0316220 A1 | 12/2012 | Ward et al. | |
| 2012/0322660 A1* | 12/2012 | Beghyn | C07K 14/43563 504/319 |
| 2014/0013471 A1 | 1/2014 | Baum et al. | |
| 2014/0093474 A1* | 4/2014 | Vander Meer | A01N 57/16 424/84 |

OTHER PUBLICATIONS

Dowling et al (Phylogenetic Origin and Diversification of RNAi Pathway Genes in Insects. Genome Biol. Evol. 8(12):3784-3793, 2016).*
Li et al (RNA Interference of Four Genes in Adult Bactrocera dorsalis by Feeding Their dsRNAs. www.plosone.org, 1-11, Mar. 2011).*
Abdel-latief et al (an epoxide hydrolase involved in the biosynthesis of an insect sex attractant and its use to localize the production site. PNAS, 8914-8919, Jul. 1, 2008).*
Chung et al (Wax, sex and the origin of species: Dual roles of insect cuticular hydrocarbons in adaptation and mating. Bioessays 37 : 822-830, 2015).*
Howard, et al.; "Ecological, Behavioral, and Biochemical Aspects of Insect Hydrocarbons"; Annu. Rev. Entomol.; vol. 50, pp. 371-393 (Sep. 7, 2004).
Zhang, et al.; "Feasibility, limitation and possible solutions of RNAi-based technology for insect pest control"; Insect Science; vol. 20, pp. 15-30 (Jun. 12, 2012).

* cited by examiner

*Primary Examiner* — Medina A Ibrahim
*Assistant Examiner* — Wayne Zhong
(74) *Attorney, Agent, or Firm* — Bozicevic Field & Francis, LLP; Paula A. Borden; Payal B. Sud

(57) ABSTRACT

The present disclosure provides interfering nucleic acids, and compositions comprising same, that reduce viability and/or activity of a pest, e.g., a Hymenoptera pest. The interfering nucleic acids and compositions are useful in controlling Hymenoptera pests, which methods are also provided.

18 Claims, 8 Drawing Sheets

Specification includes a Sequence Listing.

FIGURE 1 – TABLE 1

| | Construct Primers | Sequence |
|---|---|---|
| LH16891 | LH16891_F_T7: TAATACGACTCACTATAGGGCCGAAAGTGATGGAGAATC (SEQ ID NO:1)<br>LH16891_R_T7: TAATACGACTCACTATAGGGATCCCCAAAAGATAGTA (SEQ ID NO:2) | ATGGGATGGCAAGATATTTATAATTATAATACATACAGAATTATACAAAGCCACTAACTTGTAGAATTGGCTGTTTATAA<br>GTTCACCCTTTGGAAGTATATATTATAAACTCTTGCTTACTTGCTGTATTTGCTTCGTTCGTTGGTCTCGGTTACATGAAAA<br>ATAAGGCACCATATAAGCCTGAAATATCTAGTGGTTTGGTTTTCGAAATATACTTTTTATAGTTCTACAATAATCTCCGCTAGTG<br>CGATTAGACTCTCAATATGAGATGGTGGTTCCAGTTTGCACGTATAGCATCATCACGTGTCAGAGTAGCTTGCTGCATAT<br>TTAAGGAAAAACAGAATCAGGTTTCGAGTTTCCAGCGATAGCATCATCACGTGTCAGAGTAGCTTGCTGCATAT<br>TTTAAAATATATGTTAGACGAAAGAGAGCAACATTTATTACCTTGATTAATTGTCCGTGCATGCATGCATGTACTAGTGC<br>CATGGTAA (SEQ ID NO:3) |
| LH23306 | LH23306_F_T7: TAATACGACTCACTATAGGGCGAGATGACAGAGAAGTGGATCCACCGAAGAAGATGGCGCGTGTTAAGAC (SEQ ID NO:4)<br>LH23306_R_T7: TAATACGACTCACTATAGGGGTTTTCAACAATAAGACCTACCA (SEQ ID NO:4) | ATGAAGTATCCGAAGTTTCTTGGACAGAGAAGTGCGATCCACCGAAGAAGATGGCGCGCGTGTTAAGAC<br>ATACAATAAGTGCTACAACGTCTTTCCAAGTCGTCGGTGAACAGTTGGATCTGCCGAGACATATAGCTCCCGTT<br>GGCTGAAAAATATACCGTTCACTTGCTGGTTACAACTTATCTTTGAAACAAGATTCTCATTATAGTTGCTCAAATC<br>ATATGGTGGGGTCTTATGGTTGAAAATAGTA (SEQ ID NO:5) |
| LH17398 | LH17398_F_T7: TAATACGACTCACTATAGGGTATTCCCTGGTGGTCATGT (SEQ ID NO:6)<br>LH17398_R_T7: TAATACGACTCACTATAGGGATCGGCATTGGCATTGATTCA (SEQ ID NO:6) | GTTCAGAATCCTATTCAAGATGCAGGCGAGTAAAAGTCTGGTGGATAAGTTATATCGGGATAAATTATGGACAATCA<br>TCCGATCCGAGCTAACCTAAGCGATGGCGATGATGGACCGAAGCGTTCCGACCCTGCGCACCATCGCATGATA<br>CTATTTAGCAAGTCTCGGCGACCGAAGCTGGATGATGAAGAGTGATCGGAAACAAGAAGACCTTCGATCTCAATGGATCCTATAA<br>CATAGAAAACTTCTACAGACTTCGTCTCCGC (SEQ ID NO:7) |
| LH11439b | Bong_LH11439F2_T7: TAATACGACTCACTATAGGGACTGGTTGACTCGCCAAAAC (SEQ ID NO:7)<br>Bong_LH11439R2_T7: TAATACGACTCACTATAGGGCACTATGAGCATCAAGAACGTCGGATGAAGC (SEQ ID NO:8) | ACTGGTTGACTCGCCAAAACAAGCTAATTAACAGTTTAAATTAACATGGGCGTGGTGCCCATGGCCTGCATGTCCATGATAATGGT<br>CATGAGGAAGCGAAAGCGTTCATTCAGTTCGTTCAGCCTCAACAAGATTAGGAGCAGCCTAGCGTATACGTATACGTAATAAGCCAATACATT<br>TTATATTTCATTGCATGGCAGGAGCTCACGCGTTGGGTTCTGGTGGTGACTACTTTTAGCAAGCCTGCATCACTCACTCACCATGGTCATC<br>ACATTCTCATTTGCCGGAAGAAGACATTAGTTGAGCCTCTCCATTACGTAGCGTATATCTACTCACCATGGTCATCATC<br>GTTATGGTGGATGCGATGGGCATCAAATGGCCAGCATCGCTCCCAGATCGGCGATGGTAATCGGATGGCATGGTATGACTTCATCC<br>ACGTTCTGTGATG (SEQ ID NO:8) |
| LH18968 | LH18968_F_T7: TAATACGACTCACTATAGGGGTGTTTGTCCTCGTTATA (SEQ ID NO:9)<br>LH18968_R_T7: TAATACGACTCACTATAGGGAGGGAGGCCGAAGTCGGATCGTAGTGTCAT (SEQ ID NO:10) | ATGGGATGGCAAGATATTTAATTATTAAACTCTTGCTACTTGTATTCGTTCATCTCGTTATTGCTGCTACAATCTGCTAATATAA<br>TGGCGTCCATCTGGAAGATATATTATATATAATAAATCCTTATGCTCAGATAATCGGCTTACTTGCTACCATTGGATAGT<br>AAAGGAACAGACATATATCTAGTGGTTCAATATGGTCAGAAGCGTTTCCATCCTCTTATTATCGGATAATCACATTTATATTGTA<br>CGATTAGACTCTCAATATGAGATCCAGTCGTTCGAGTATCCACAGTTCACAGGGCCTAAGGCTAGGTATATTGGTTCGAGCTCATGT<br>TTAAGGAAAACAGATCGTTTACGAGCCAGAGAGTAAGACATCAATTATTGGATTATACCCTCAAGGTCATCCAAAAGCG<br>CATGGTAA (SEQ ID NO:11) |
| LH11831 | T7_LH11831_F: TAATACGACTCACTATAGGGTGTTAGCTTCCGGCTCT (SEQ ID NO:11)<br>T7_LH11831_R: TAATACGACTCACTATAGGGGTGCACAAGAACAGTTAATCAAGG (SEQ ID NO:12) | CCACTAACTGCAATGCAATGGCCGAATATGGCCGATTATAAGTTCACCCTTCGAAGTTACATTATAACTCTGGTACTTGCGT<br>TAGCTTCCGGCTCTGTGTACATTGGTACAGGAAAAATAAACAACCATATAAGCTGAAAACCTTAATATTGTTACAATATA<br>ATGCAAATATTGCGAAACATTGGGATAGTGAAACAACAACACATAACTAAGGTTTTGGAAATACAATAACTTATGA<br>TGTTTACATCAGATCCAACCTGCGCTAGTGCAATTAGACTTCTTCTTCTAATTGGTGTGGAATTCTTATATTGAAAATT<br>TTAGGATTATCTTGAAACCTGATATCTTGTTAAGGAAAAAATACAGAATCAGGTTCTGGTTCTGCATGTATACCCAT<br>CACGTGTCAAACGGAGCTTCATCGTGAATTTATGTATATTATTTTTGGCTGGTGGAAGATTATTATTCAAAAATTCC<br>TAATTGTCTCGTGGATATCTGGTCATGAATTTATGCATGAAGAGAAAATCTCAAAACCTTCAAAAAGTCCC<br>TCCTATTAAACTATATAAAGCAGCCATGGCCCTCTGCAATCCTACAAAACCAGATTCCTACGATTAATCAATGGCTGTGTCTGGAATATCTCCCTGAT<br>CATTCAGTTCTGGAATAAGGTCAATCCTACAAACCAGATTCCTGCTTTATTCATTGGTCTTTATTCATTCATGAATGCT (SEQ ID NO:13) |

SEQUENCE LISTING

```
<160> NUMBER OF SEQ ID NOS: 41

<210> SEQ ID NO 1
<211> LENGTH: 40
<212> TYPE: DNA
<213> ORGANISM: Artificial Sequence
<220> FEATURE:
<223> OTHER INFORMATION: synthetic polynucleotide sequence

<400> SEQUENCE: 1
taatacgact cactataggg gccgaaagtg atggagaatc                            40

<210> SEQ ID NO 2
<211> LENGTH: 40
<212> TYPE: DNA
<213> ORGANISM: Artificial Sequence
<220> FEATURE:
<223> OTHER INFORMATION: synthetic polynucleotide sequence

<400> SEQUENCE: 2
taatacgact cactataggg atcgccgcca aaagatagta                            40
```

-continued

<210> SEQ ID NO 3
<211> LENGTH: 44
<212> TYPE: DNA
<213> ORGANISM: Artificial Sequence
<220> FEATURE:
<223> OTHER INFORMATION: synthetic polynucleotide sequence

<400> SEQUENCE: 3
taatacgact cactataggg cgacatacat aaagtgctac aacg                          44

<210> SEQ ID NO 4
<211> LENGTH: 42
<212> TYPE: DNA
<213> ORGANISM: Artificial Sequence
<220> FEATURE:
<223> OTHER INFORMATION: synthetic polynucleotide sequence

<400> SEQUENCE: 4
taatacgact cactataggg ttttcaacaa taagacccac ca                            42

<210> SEQ ID NO 5
<211> LENGTH: 40
<212> TYPE: DNA
<213> ORGANISM: Artificial Sequence
<220> FEATURE:
<223> OTHER INFORMATION: synthetic polynucleotide sequence

<400> SEQUENCE: 5
taatacgact cactataggg tatttccctg gtggtcatcc                               40

<210> SEQ ID NO 6
<211> LENGTH: 40
<212> TYPE: DNA
<213> ORGANISM: Artificial Sequence
<220> FEATURE:
<223> OTHER INFORMATION: synthetic polynucleotide sequence

<400> SEQUENCE: 6
taatacgact cactataggg atcggcattg ttttgattcc                               40

<210> SEQ ID NO 7
<211> LENGTH: 40
<212> TYPE: DNA
<213> ORGANISM: Artificial Sequence
<220> FEATURE:
<223> OTHER INFORMATION: synthetic polynucleotide sequence

<400> SEQUENCE: 7
taatacgact cactataggg actggttgac tcgccaaaac                               40

<210> SEQ ID NO 8
<211> LENGTH: 40
<212> TYPE: DNA
<213> ORGANISM: Artificial Sequence
<220> FEATURE:
<223> OTHER INFORMATION: synthetic polynucleotide sequence

<400> SEQUENCE: 8
taatacgact cactataggg catcagaacg tggatgaagc                               40

<210> SEQ ID NO 9
<211> LENGTH: 40
<212> TYPE: DNA
<213> ORGANISM: Artificial Sequence
<220> FEATURE:

<223> OTHER INFORMATION: synthetic polynucleotide sequence

<400> SEQUENCE: 9
taatacgact cactataggg tcgttttggt cctcgttaca          40

<210> SEQ ID NO 10
<211> LENGTH: 40
<212> TYPE: DNA
<213> ORGANISM: Artificial Sequence
<220> FEATURE:
<223> OTHER INFORMATION: synthetic polynucleotide sequence

<400> SEQUENCE: 10
taatacgact cactataggg ggcgaagttg gatgtggtat          40

<210> SEQ ID NO 11
<211> LENGTH: 40
<212> TYPE: DNA
<213> ORGANISM: Artificial Sequence
<220> FEATURE:
<223> OTHER INFORMATION: synthetic polynucleotide sequence

<400> SEQUENCE: 11
taatacgact cactataggg tcgttcttag cttcggtcct          40

<210> SEQ ID NO 12
<211> LENGTH: 42
<212> TYPE: DNA
<213> ORGANISM: Artificial Sequence
<220> FEATURE:
<223> OTHER INFORMATION: synthetic polynucleotide sequence

<400> SEQUENCE: 12
taatacgact cactataggg tgcacagaac aattaatcaa gg          42

<210> SEQ ID NO 13
<211> LENGTH: 543
<212> TYPE: DNA
<213> ORGANISM: Linepithema humile

<400> SEQUENCE: 13
atgggatggc aagatattta taattattac atactagaat tatcaaagcc actaactcgc      60
aattggctgt ttataagttc accttttcgaa gttatattta aactcttgc ttacttgtat     120 ttcgttcttc gttttggtcc tcgttacatg aaaaataagc caccatataa gctgaaaacc     180
tttatattgg tctacaatat aattcaaata ttggcaaaca tttgggtagt aaaggaacac     240
atatctagtg gttggttttc gaaatatact tttttatgtt ttataccaca tccaacttcg     300
cctagtgcga ttagactctt caatatgatg tggtggtttc tactattgaa attttttgat     360
tattttgaaa cctgtatatt tgtgttaagg aaaaaacaga atcaggtttc cagtttgcac     420
gtataccatc acgtgtcaaa cgtagctttc gcctggtatt ttttaaaata tatgttagac     480
gaaagagcaa catttattac cttgattaat tgttccgtgc atgtaatact agtgccatgg     540
taa                                                                   543

<210> SEQ ID NO 14
<211> LENGTH: 255
<212> TYPE: DNA
<213> ORGANISM: Linepithema humile

<400> SEQUENCE: 14
atgaagttat ccgaagtgtt tgcttggaca gaacaagtcg atccacgaac gaaggattgg      60
ccgctgttaa cgacatacat aaagtgctac aacgtcttcc aagtcgtggt gaacagttgg    120
ctggtgcgag aacatatagc tgccggttgg ctgaaaaata taccgttcac ttgtgtggtt    180
acaacttatt cttacgaatt tcctcattat aagtttgctc aaatcatatg gtgggtctta    240
ttgttgaaaa tagta                                                     255

<210> SEQ ID NO 15
<211> LENGTH: 255
<212> TYPE: DNA
<213> ORGANISM: Linepithema humile

<400> SEQUENCE: 15
atttcagatc ctattcaaga tgacgagcgc agtaacaagt ctggtggata gttatagaga     60
cattatggac aatcagtccg atcccagggt aaacgattgg gcgatgatga gcagccgtt    120 tccgaccctg gcgatatgca tctcatacgc ttactttagc aaagttctgg gaccgaagct    180
gatggaaaac agaaagcctt tcgatcttcg ggggatcctc ataacataca accttctaca    240
gactttcttc tccgc                                                     255

<210> SEQ ID NO 16
<211> LENGTH: 463
<212> TYPE: DNA
<213> ORGANISM: Linepithema humile

<400> SEQUENCE: 16
actggttgac tcgccaaaac caacgttaat atatacgatg ttatatctgc tcatcgtttg     60
ggcgggtcct aaggtcatga ggaagcgaaa agcttttaaa ttaacatggg cgctggtgcc    120
ctacaatctt gccatggcct gtcttaatgc ttatatttcc attcagttgc ttctagcctc    180
aacaagatta cgatatagtt acgtatgcca gccaataagg cacattacgc gtcccgacga    240
gcttcagatt gctcacgcgg tttggtggta ctactttagc aagcttctgg aattctgcga    300
cacattcttc ttcattttgc ggaagaaaga caatcagttg agcttcctcc acgtctatca    360
tcactccacc atgttctcgt tatggtggat cggcatcaaa tgggtgccga gtggatcgac    420
tttcctgcca gcgatggtga atagcttcat ccacgttctg atg                      463

<210> SEQ ID NO 17
<211> LENGTH: 543
<212> TYPE: DNA
<213> ORGANISM: Linepithema humile

<400> SEQUENCE: 17
atgggatggc aagatattta taattattac atactagaat tatcaaagcc actaactcgc     60
aattggctgt ttataagttc acctttcgaa gttatattta taactcttgc ttacttgtat    120
ttcgttcttc gttttggtcc tcgttacatg aaaaataagc caccatataa gctgaaaacc    180
tttatattgg tctacaatat aattcaaata ttggcaaaca tttgggtagt aaaggaacac    240
atatctagtg gttggttttc gaaatatact tttttatgtt ttataccaca tccaacttcg    300
cctagtgcga ttagactctt caatatgatg tggtggtttc tactattgaa attttttgat    360
tattttgaaa cctgtatatt tgtgttaagg aaaaaacaga atcaggtttc cagtttgcac    420
gtataccatc acgtgtcaaa cgtagctttc gcctggtatt ttttaaaata tatgttagac    480
gaaagagcaa catttattac cttgattaat tgttccgtgc atgtaaatact agtgccatgg    540 taa                                                                  543

<210> SEQ ID NO 18
<211> LENGTH: 750
<212> TYPE: DNA
<213> ORGANISM: Linepithema humile

<400> SEQUENCE: 18

```
ccactaactc gcaattggcc gattataagt tcacctttcg aagttacatt tataactctt      60
gcttacttgt atttcgttct tagcttcggt cctcgctaca tgaaaaataa accaccatat     120
aagctgaaaa ccttcatatt agtctacaat ataatgcaaa tattggcaaa catttggata     180
gtaaaagaac ataactaa tggttggttt tcgaaatata cttttagatg ttttacatca      240
gatccaactt cgcctagtgc aattagactc ttcaatttgg tgtggtggat tctattattg     300
aaattttag attatcttga aacctgtata tttgtgttaa gaaaaaaaca gaatcaggtt      360
tctggtttgc atgtatacca tcacgtgtca aacgtagctt tcatctggta ttttttaaaa     420
tattatttag acgaaagatt aacatttatt cccttgatta attgttctgt gcatgtaatt     480
atgtatattt attatttttt ggctgcgtgg aattcaaaac ttcaaaaaag tctcctccct     540
attaaactat atataacaag gatacaattg atggatccag ttagcgctac tgtacggcct     600
agagaaagcg tcgtacgaaa aacgacggca tggcctctct caggcttctt tctgctgtta     660
tttaatcaat gggcttgtct ggaatacatt tcagttctgg aatacggtca atcctacaaa     720
ccagattcct tggctttatt catgaatgct                                      750
```

<210> SEQ ID NO 19
<211> LENGTH: 11
<212> TYPE: PRT
<213> ORGANISM: Artificial Sequence
<220> FEATURE:
<223> OTHER INFORMATION: synthetic amino acid sequence

<400> SEQUENCE: 19

Tyr Gly Arg Lys Lys Arg Arg Gln Arg Arg Arg
1               5                   10

<210> SEQ ID NO 20
<211> LENGTH: 12
<212> TYPE: PRT
<213> ORGANISM: Artificial Sequence
<220> FEATURE:
<223> OTHER INFORMATION: synthetic amino acid sequence

<400> SEQUENCE: 20

Arg Arg Gln Arg Arg Thr Ser Lys Leu Met Lys Arg
1               5                   10

<210> SEQ ID NO 21
<211> LENGTH: 27
<212> TYPE: PRT
<213> ORGANISM: Artificial Sequence
<220> FEATURE:
<223> OTHER INFORMATION: synthetic amino acid sequence

<400> SEQUENCE: 21

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 22
<211> LENGTH: 33

```
<212> TYPE: PRT
<213> ORGANISM: Artificial Sequence
<220> FEATURE:
<223> OTHER INFORMATION: synthetic amino acid sequence

<400> SEQUENCE: 22

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 23
<211> LENGTH: 16
<212> TYPE: PRT
<213> ORGANISM: Artificial Sequence
<220> FEATURE:
<223> OTHER INFORMATION: synthetic amino acid sequence

<400> SEQUENCE: 23

Arg Gln Ile Lys Ile Trp Phe Gln Asn Arg Arg Met Lys Trp Lys Lys
1               5                   10                  15

<210> SEQ ID NO 24
<211> LENGTH: 11
<212> TYPE: PRT
<213> ORGANISM: Artificial Sequence
<220> FEATURE:
<223> OTHER INFORMATION: synthetic amino acid sequence

<400> SEQUENCE: 24

Tyr Gly Arg Lys Lys Arg Arg Gln Arg Arg Arg
1               5                   10

<210> SEQ ID NO 25
<211> LENGTH: 9
<212> TYPE: PRT
<213> ORGANISM: Artificial Sequence
<220> FEATURE:
<223> OTHER INFORMATION: synthetic amino acid sequence

<400> SEQUENCE: 25

Arg Lys Lys Arg Arg Gln Arg Arg Arg
1               5

<210> SEQ ID NO 26
<211> LENGTH: 11
<212> TYPE: PRT
<213> ORGANISM: Artificial Sequence
<220> FEATURE:
<223> OTHER INFORMATION: synthetic amino acid sequence

<400> SEQUENCE: 26

Tyr Gly Arg Lys Lys Arg Arg Gln Arg Arg Arg
1               5                   10

<210> SEQ ID NO 27
<211> LENGTH: 8
<212> TYPE: PRT
<213> ORGANISM: Artificial Sequence
<220> FEATURE:
<223> OTHER INFORMATION: synthetic amino acid sequence

<400> SEQUENCE: 27

Arg Lys Lys Arg Arg Gln Arg Arg
1               5
```

<210> SEQ ID NO 28
<211> LENGTH: 11
<212> TYPE: PRT
<213> ORGANISM: Artificial Sequence
<220> FEATURE:
<223> OTHER INFORMATION: synthetic amino acid sequence

<400> SEQUENCE: 28

Tyr Ala Arg Ala Ala Ala Arg Gln Ala Arg Ala
1               5                   10

<210> SEQ ID NO 29
<211> LENGTH: 11
<212> TYPE: PRT
<213> ORGANISM: Artificial Sequence
<220> FEATURE:
<223> OTHER INFORMATION: synthetic amino acid sequence

<400> SEQUENCE: 29

Thr His Arg Leu Pro Arg Arg Arg Arg Arg Arg
1               5                   10

<210> SEQ ID NO 30
<211> LENGTH: 11
<212> TYPE: PRT
<213> ORGANISM: Artificial Sequence
<220> FEATURE:
<223> OTHER INFORMATION: synthetic amino acid sequence

<400> SEQUENCE: 30

Gly Gly Arg Arg Ala Arg Arg Arg Arg Arg Arg
1               5                   10

<210> SEQ ID NO 31
<211> LENGTH: 647
<212> TYPE: DNA
<213> ORGANISM: Solenopsis invicta
<220> FEATURE:
<221> NAME/KEY: misc_feature
<222> LOCATION: (605)..(605)
<223> OTHER INFORMATION: n is a, c, g, or t

<400> SEQUENCE: 31
aagtgacgca cactaccaga attctgttaa cagattttac acaacaatgg cgccgaatat      60
aacaattaaa tcaacaggag tactattcga agatgagact cttggcgaac cgcaagtagt     120
tgaagagctg aaggataaat ctaaatatgt taggcgcatt gagtggaaaa gagtaatatt     180
tttctcgttt ctacatctcg gtgccctttt cggcgtttat cttttattca catctgtcaa     240
atttgctacc attttatttg taattttctt atctgaaatc agcttgatgg gaatcacagc     300
tggaaatcat cgactgtggg cacaccgatc ttataaagcc aagtggcctc tccagctgct     360
gcttgttatt atgagcacta tagcgtttca gttcgatgtg atccattggt ccagagatca     420
tagggttcac cacaaataca gtgaaactga cgccgatccg cataatgcta aaagaggttt     480
cttcttcgca catgtgggct ggctggtttg caggaaacat tcagaagtca agaaaaaagg     540
caaagaaatt gacataagcg atcttgaaag caatccaata ttagcattcc aaaagaaata     600
ttatnaacat actggtgcta ttgctctgct ttattttacc aaccgtc                    647

<210> SEQ ID NO 32
<211> LENGTH: 20
<212> TYPE: DNA
<213> ORGANISM: Artificial Sequence

```
<220> FEATURE:
<223> OTHER INFORMATION: synthetic polynucleotide sequence

<400> SEQUENCE: 32
atgcggtcat gttccttttc                                              20

<210> SEQ ID NO 33
<211> LENGTH: 20
<212> TYPE: DNA
<213> ORGANISM: Artificial Sequence
<220> FEATURE:
<223> OTHER INFORMATION: synthetic polynucleotide sequence

<400> SEQUENCE: 33
ttgtccttcg agtgatgctg                                              20

<210> SEQ ID NO 34
<211> LENGTH: 20
<212> TYPE: DNA
<213> ORGANISM: Artificial Sequence
<220> FEATURE:
<223> OTHER INFORMATION: synthetic polynucleotide sequence

<400> SEQUENCE: 34
tgcttggaca gaacaagtcg                                              20

<210> SEQ ID NO 35
<211> LENGTH: 20
<212> TYPE: DNA
<213> ORGANISM: Artificial Sequence
<220> FEATURE:
<223> OTHER INFORMATION: synthetic polynucleotide sequence

<400> SEQUENCE: 35
ccaaccggca gctatatgtt                                              20

<210> SEQ ID NO 36
<211> LENGTH: 20
<212> TYPE: DNA
<213> ORGANISM: Artificial Sequence
<220> FEATURE:
<223> OTHER INFORMATION: synthetic polynucleotide sequence

<400> SEQUENCE: 36
ggcgtcatca actccttcat                                              20

<210> SEQ ID NO 37
<211> LENGTH: 20
<212> TYPE: DNA
<213> ORGANISM: Artificial Sequence
<220> FEATURE:
<223> OTHER INFORMATION: synthetic polynucleotide sequence

<400> SEQUENCE: 37
atggtggtca ggtgcttctt                                              20

<210> SEQ ID NO 38
<211> LENGTH: 20
<212> TYPE: DNA
<213> ORGANISM: Artificial Sequence
<220> FEATURE:
<223> OTHER INFORMATION: synthetic polynucleotide sequence

<400> SEQUENCE: 38
attcagttca cgaccgcttt                                              20
```

```
<210> SEQ ID NO 39
<211> LENGTH: 20
<212> TYPE: DNA
<213> ORGANISM: Artificial Sequence
<220> FEATURE:
<223> OTHER INFORMATION: synthetic polynucleotide sequence

<400> SEQUENCE: 39
ccttggcctt tatcctctcc                                              20

<210> SEQ ID NO 40
<211> LENGTH: 20
<212> TYPE: DNA
<213> ORGANISM: Artificial Sequence
<220> FEATURE:
<223> OTHER INFORMATION: synthetic polynucleotide sequence

<400> SEQUENCE: 40
accacatcca acttcgccta                                              20

<210> SEQ ID NO 41
<211> LENGTH: 20
<212> TYPE: DNA
<213> ORGANISM: Artificial Sequence
<220> FEATURE:
<223> OTHER INFORMATION: synthetic polynucleotide sequence

<400> SEQUENCE: 41
acgtgcaaac tggaaacctg                                              20
```

COMPOSITIONS AND METHODS FOR CONTROLLING PESTS

CROSS-REFERENCE

This application claims the benefit of U.S. Provisional Patent Application No. 61/983,364, filed Apr. 23, 2014, which application is incorporated herein by reference in its entirety.

INCORPORATION BY REFERENCE OF SEQUENCE LISTING PROVIDED AS A TEXT FILE

A Sequence Listing is provided herewith as a text file, "BERK-238WO SeqList_ST25.txt" created on Apr. 22, 2015 and having a size of 13 KB. The contents of the text file are incorporated by reference herein in their entirety.

INTRODUCTION

Argentine ants are a widespread and serious pest in residences, businesses, and agricultural areas. Argentine ants often enter structures in search of food or water or while fleeing environmental disturbances such as flooded nests, cold temperatures, or hot, dry weather. Unlike other ant species, invasive Argentine ant colonies often contain numerous queens and interconnected nests and thus eliminating a single queen does not prevent a colony from continuing to breed. When colonizing new areas Argentine ants readily form super colonies from only a small number of founder ants. Due to this massive population expansion from only a few individuals, Argentine ants often remain closely related, sharing similar genetics and similar pheromones. Genetically dissimilar ant colonies are generally territorial, fighting each other and inhibiting population expansion. Colonies of genetically similar invasive Argentine ants do not show aggressive behavior toward one another and thus their expansion is not repressed by territoriality like colonies in native regions.

The aggressive territoriality of Argentine ants can displace native fauna thus having a devastating impact on natural biodiversity affecting both native plants and animals. For example, Argentine ants have displaced California harvester ant (*Pogonomyrmex califomicus*) populations in southern California, impacting animals that feed on the harvester ants such as the coast horned lizard (*Phrynosoma coronatum*). Displacement of native fauna, such as beneficial insects, can negatively impact agricultural production. Further still, Argentine ants often promote the propagation of crop destroying aphids through a symbiotic relationship wherein the ants feed on the "honeydew" secreted by the aphids.

Conventional pest control methods are often ineffective against Argentine ants. Application of pesticide sprays and boiling water is often impractical for destroying colonies because, unlike mounding ants, Argentine ant nests are often diffuse and spread over a large area. Exaggerating the problem, spraying colonies with pesticides has been shown to occasionally stimulate egg-laying in the queens of the sprayed colonies. Feeding low concentrations of slow-acting poison bait can be effective when bait is carried back to the colonies and shared with the queens. However, poison bait feeding can take days to eradicate a colony and the poison bait presents an environmental contaminate and hazard that may be ingested by unintended non-target organisms.

SUMMARY

The present disclosure provides interfering nucleic acids, and compositions comprising same, that reduce viability and/or activity of a pest, e.g., a Hymenoptera pest. The interfering nucleic acids and compositions are useful in controlling Hymenoptera pests, which methods are also provided.

BRIEF DESCRIPTION OF THE DRAWINGS

FIG. 1 provides Table 1 which lists the primers used to generate the Elongase targeting RNAi constructs and the targeted Elongase sequences (from top to bottom then left to right SEQ ID NOs: 1-18).

DEFINITIONS

Figure 2:
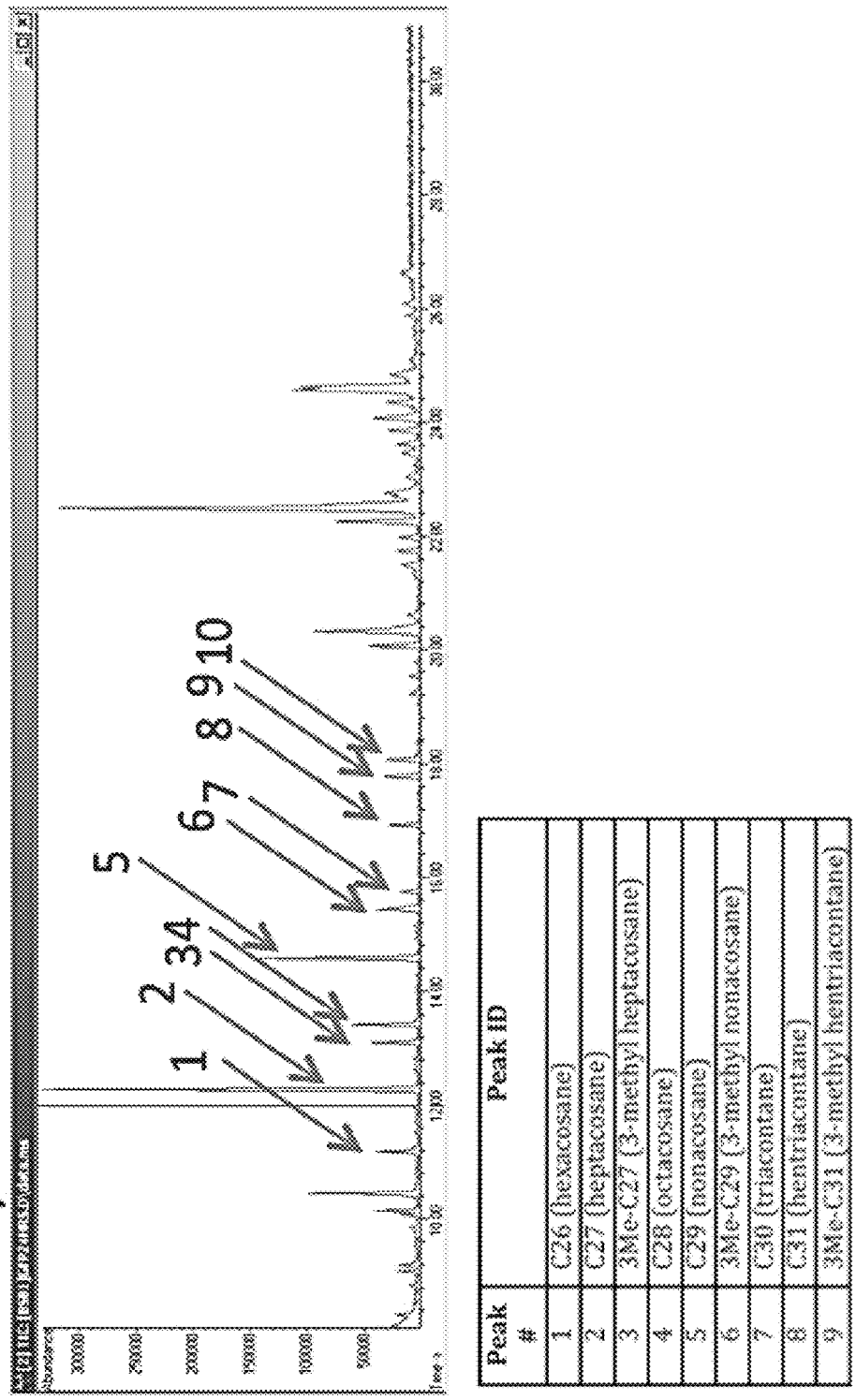
FIG. 2 depicts chemicals present in ants following control RNAi feeding as detected by gas-chromatography-mass spectrometry.

The term "pheromones" as used herein refers to secreted or excreted chemical factors that affect organism behavior, e.g., social behavior. Pheromones can be volatile or non-volatile. Non-volatile pheromones may represent cuticular contact pheromones which are used by organisms to communicate through contact with one another, e.g., through the cuticle to cuticle contact. For example, cuticular pheromones, particularly as they pertain to insects, are often made, at least in part of, cuticular hydrocarbons (CHCs). CHCs that are necessary for insect communication, e.g., nestmate recognition or mate recognition, are well known in the art, see, e.g., Blomquist, & Bagnères (2010) Insect Hydrocarbons: Biology, Biochemistry, and Chemical Ecology. New York: Cambridge University Press and Howard, R. W., and Blomquist (2005) *Annu Rev Entomol*, 50:371-393, the disclosures of which are incorporated by reference herein. Insect pheromones are classically classified as primers or releasers, and in many cases CHCs are releasers, e.g., pheromones that cause immediate reversible changes in behavior of the target organism.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an interfering nucleic acid" includes a plurality of such nucleic acids and reference to "the Hymenoptera pest" includes reference to one or more Hymenoptera pests and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Aspects of the present disclosure include interfering nucleic acids for controlling Argentine ants, compositions including such interfering nucleic acids, and methods for controlling argentine ants through the use of interfering nucleic acids. According to certain embodiments, as described in more detail below, interfering nucleic acids of the present disclosure include interfering nucleic acids useful in inhibiting transcription, e.g., reducing gene expression, or translation of one or more target genes in a host organism. Additional embodiments include nucleic acids, expression vectors, bacteria, plants, and other organisms comprising such interfering nucleic acids.

In certain embodiments, the interfering nucleic acid of the present disclosure is designed to target a target gene in a host organism. Target genes of the present disclosure include any gene that is necessary for the health, survival, or propagation of individual organisms or populations of individual organisms. For example, target genes of the present disclosure may include any gene that is necessary for the health, survival, or propagation of an individual Hymenoptera host or populations of individual Hymenoptera hosts, e.g., colonies of individual Hymenoptera hosts. As used herein in reference to Hymenoptera hosts, the term "population" refers to any convenient or appropriate group of individuals including but not limited to, e.g., a brood, a colony, a group of colonies (e.g., interconnected colonies), a subpopulation of a colony, a subpopulation of a group of colonies, etc. In certain embodiments, target genes of the present disclosure include genes involved in cuticular hydrocarbon synthesis. For example, target genes of the present disclosure include elongase genes or desaturase genes.

Aspects of the present disclosure also include compositions comprising interfering nucleic acids as described herein. In certain embodiments, such compositions of the present disclosure include spray compositions, liquid compositions, solid compositions, and semi-solid compositions. Compositions of the present disclosure may include or may be in the from of a food source, e.g., a food source for a host organism, e.g., a food source for a Hymenoptera host, e.g., a food source for a ant, e.g., a food source for an Argentine ant. In certain instances, compositions of the present disclosure may include or may be in the form of nectar, e.g., nectar for a host organism, e.g., nectar for a Hymenoptera host, e.g., nectar for an ant, e.g., nectar for an Argentine ant. In certain embodiments, compositions of the present disclosure include an attractant, e.g., a chemical, synthetic, or natural agent, e.g., a foodstuff, useful in attracting a host organism to consume or stimulating a host organism to consume a composition of the invention. In certain embodiments, compositions of the present disclosure include a phagostimulant, e.g., a chemical, synthetic, or natural agent, e.g., a foodstuff, useful in stimulating a host organism to consume or stimulating a host organism to consume a greater amount of a composition of the invention. Such phagostimulants of the present disclosure can be any agent useful in stimulating a host organism to consume more of a composition than would be consumed if the composition did not contain the agent.

Aspects of the present disclosure include methods of reducing viability and/or activity of a host organism or a population of host organisms by introducing an effective amount of an interfering nucleic acid as described herein. In certain embodiments, methods are presented for reducing the viability and/or activity of a Hymenoptera host, e.g., an ant, e.g., an Argentine ant, by introducing an effective amount of an interfering nucleic acid as described herein. In certain embodiments, methods of the present disclosure include methods reducing viability and/or activity of a host organism, e.g., a Hymenoptera host, by introducing an interfering nucleic acid as described herein effective to reduce nestmate recognition, queen recognition, larvae recognition, egg recognition, desiccation resistance, and microbial resistance. In certain instances, methods of the present disclosure reduce more than one of, e.g., two of, or more than two of, or three of, or more than three of, or four of, or more than four of, or five of, or more than five of, of six of, nestmate recognition, queen recognition, larvae recognition, egg recognition, desiccation resistance, and microbial resistance of a host organism, e.g., a Hymenoptera host, e.g., an ant, e.g., an Argentine ant.

Interfering Nucleic Acid

The present disclosure provides interfering nucleic acids, and compositions comprising such interfering nucleic acids, which interfering nucleic acids reduce viability and/or activity of a pest.

The terms "double stranded RNA," "dsRNA," "partial-length dsRNA," "full-length dsRNA," "synthetic dsRNA," "in vitro produced dsRNA," "in vivo produced dsRNA," "bacterially produced dsRNA," "isolated dsRNA," and "purified dsRNA" as used herein refer to nucleic acid molecules capable of being processed to produce a smaller nucleic acid, e.g., a short interfering RNA (siRNA), capable of inhibiting or down regulating gene expression, for example by mediating RNA interference "RNAi" or gene silencing in a sequence-specific manner Design of a dsRNA or a construct comprising a dsRNA targeted to a gene of interest is routine in the art, see e.g., Timmons et al. (2001) *Gene*, 263:103-112; Newmark et al. (2003) *Proc Natl Acad Sci USA*, 100 Supp 1:11861-5; Reddien et al. (2005) *Developmental Cell*, 8:635-649; Chuang & Meyerowitz (2000) *Proc Natl Acad Sci USA*, 97:4985-90; Piccin et al. (2001) *Nucleic Acid Res*, 29:E55-5; Kondo et al. (2006) *Genes Genet Syst*, 81:129-34; and Lu et al. (2009) *FEBS J*, 276: 3110-23; the disclosures of which are incorporated herein by reference.

dsRNA may be produced de novo or may be produced from "dsRNA templates", i.e., nucleic acid templates for generating a dsRNA targeted to a particular gene. A dsRNA template or a construct for generating a dsRNA targeted to a particular gene are obtained by any convenient method and need not necessarily be comprised of RNA, e.g., a dsRNA template may be DNA, e.g., single stranded DNA or double stranded DNA. dsRNA templates may be obtained by generating a copy of a naturally occurring spliced mRNA, e.g., a cDNA, using molecular techniques, e.g., reverse transcription or first strand synthesis. dsRNA templates may also be obtained by producing a copy of the coding region, e.g. the CDS, of a gene sequence obtained from sequencing data, e.g., publicly available databases of transcriptome and genomic sequences (see e.g., genomic information from the National Center for Biotechnology Information (NCBI) available on the internet at www(dot)ncbi(dot)nlm(dot)nih(dot)gov/genome/browse/; transcriptome information at the Exon Bioinformatics for Discovery available at http://exon(dot)niaid(dot)nih(dot)gov/transcriptome(dot)html; Zeng & Extavour (2012) *Database*, bas048; and Wurm et al. (2009) *BMC Genomics*, 10:5, the disclosures of which are incorporated herein by reference), de novo sequencing of isolated nucleic acid, predicted gene sequences generated by gene prediction software (e.g., ATGpr, AUGUSTUS, BGF, DIOGENES, Dragon Promoter Finder, EUGENE, FGENESH, FRAMED, GENIUS, geneid, GENEPARSER, GeneMark, GeneTrack, GENOMESCAN, GENSCAN, GLIMMER, GLIMMERHMM, GrainEXP, MORGAN, NIX, NNPP, NNSPLICE, ORF FINDER, Regulatory Sequence Analysis Tool, SPLICEPREDICTOR, VEIL, and the like), and the like. Such first and iterative copies of dsRNA templates may represent the same sequence, e.g., the same sequence in the same 5' to 3' orientation as the sequence from which the copy was generated, or may represent the complement, the reverse, or the reverse complement of the sequence from which the copy was generated as methods for producing subsequent copies or modifying sequence orientation are well known in the art. In certain instances, a mRNA or a coding region of a gene is constructed from the genomic locus of a gene by assembly of all or some, e.g., about 1 or more, about 2 or more, about 3 or more, about 4 or more, about half, more than half, about 75% or more, about 80% or more, about 90% or more, of the exons of the genetic locus into a synthetic mRNA sequence or synthetic cDNA sequence and the resulting sequence is used to generate synthetic mRNA or synthetic cDNA. Assembly of exons of a genetic locus is routine in the art and can performed by identifying exon-intron junctions either manually or with the help of software that identifies exon-intron junctions either automatically or through user input.

In certain instances, the dsRNA template is a full-length dsRNA template and therefore the dsRNA generated from the template is a full-length dsRNA. By "full-length dsRNA" is meant a dsRNA that comprises the full length sequence of a gene, e.g., all of the coding exons of a gene, all of the coding exons of a gene including 5' or 3' untranslated regions of a gene, all of a gene sequence contained between the start codon of a gene and the stop codon of the same gene, etc. In other cases, the dsRNA template is a full-length dsRNA template but is used only to generate a partial-length dsRNA. By partial dsRNA is meant any dsRNA of a gene that contains fewer than all of the coding exons of a gene, e.g., all of a gene except for a portion of an exon, all of a gene except one exon of the gene, all of a gene except more than one exon of a gene, all of a gene except more than two exons of a gene, all of a gene except more than three exons of a gene, all of a gene except more than four exons of a gene, or all of a gene except more than five exons of a gene. Partial-length dsRNA may also represent a dsRNA that includes only a percent portion of the full-length dsRNA of a particular gene but retains the function of activating gene specific silencing by RNAi, e.g., about 95%, about 90%, about 80%, about 70%, about 60%, about 50%, about 40%, about 30%, about 20%, about 10%, about 5%, about 3%, about 2%, about 1%, about, or less than 1% of a full-length dsRNA of a particular gene. In still other instances a partial-length dsRNA template is used to generate a partial-length dsRNA, i.e., partial-length dsRNA is generated from a partial gene sequence or clone and need not be generated from a full-length sequence or clone.

In certain instances, a dsRNA template is cloned, with or without alteration of the dsRNA template sequence, and cloned or inserted into a vector, e.g., a plasmid or phage DNA, to generate a dsRNA construct. By "alteration of the dsRNA templates sequence" is meant that the dsRNA template sequence is modified either directly by introducing mutations, e.g., point mutations, insertions, deletions, silent mutations, and the like, to the original dsRNA template sequence obtained. Alteration of the dsRNA template sequence may result in a mutated dsRNA template sequence that shares about 95%, about 90%, about 80%, about 70%, about 60%, about 50%, or less than about 50% homology with the original dsRNA template sequence. In other instances, the original dsRNA template sequence obtained may be left unmutated or not mutated and one or more nucleotides may be attached to the ends of the original dsRNA template sequence, or some combination therein. In certain instances, an unmutated dsRNA template is amended with additional nucleotides that contain functional sequences, i.e., sequences that may be used for downstream applications of the dsRNA template, e.g., enzyme recognition sites including polymerase recognition sites or endonuclease recognition sites or recombination sites. Methods of nucleic acid cloning and transform which find use in cloning and transforming dsRNA templates are known in the art; see, e.g., Fire et al. (1990) *Gene,* 93:189-198; Timmons et al. (2001) *Gene,* 263:103-112; Newmark et al. (2003) *Proc Natl Acad Sci USA,* 100 Supp 1:11861-5; Reddien et al. (2005) *Developmental Cell,* 8:635-649; Chuang & Meyerowitz (2000) *Proc Natl Acad Sci USA,* 97:4985-90; Piccin et al. (2001) *Nucleic Acid Res,* 29:E55-5; and Kondo et al. (2006) *Genes Genet Syst,* 81:129-34; the disclosures of which are incorporated herein by reference.

In some embodiments, the dsRNA template, e.g., dsRNA template inserted into a vector, is transformed into a host cell specifically designed for the production of dsRNA. For example, the host cell into which the dsRNA template is transformed may be a host cell deficient in one or more processes that disrupts the production of dsRNA. In certain embodiments, the host cell is a bacterial strain deficient in an enzyme that cleaves dsRNA, e.g., an RNase enzyme or an RNaseIII enzyme. For example, the host cell may have a mutated RNase gene wherein the RNase gene is mutated by a point mutation, a frameshift mutation, or an insertion mutation. In certain embodiments, the RNase gene of the host cell is mutated by insertional mutagenesis by insertion of a polynucleotide into the coding region of the RNase gene such that the presence of the polynucleotide, and thus the presence of mutated RNase, may be selected for. In certain embodiments, the host cell is a bacterial strain with an RNaseIII gene mutated by insertion of an antibiotic resistance gene, e.g., a tetracycline gene, into the coding region of the RNaseIII, e.g., a HT115 bacterial strain, see, e.g., Timmons et al. (2001) *Gene,* 263:103-112, the disclose of which is incorporated by reference herein.

In certain instances, a dsRNA construct, e.g., a cloned dsRNA or a cloned dsRNA template that has been introduced into a vector, e.g., a plasmid or phage DNA, is used to generate dsRNA. dsRNA constructs, e.g., dsRNA plasmid constructs, may be used to generate in vitro transcribed dsRNA through the use of an in vitro transcription reaction, e.g., through the use of an in vitro transcription kit or a dsRNA synthesis kit, non-limiting examples of commercially available in vitro transcription kits and dsRNA synthesis kit include MEGAscript® RNAi Kits (Life Technologies, Grand Island, N.Y.), Replicator RNAi Kits (Thermo Scientific®, a division of Fisher Scientific®, Pittsburgh, Pa.), T7 RiboMAX™ (Promega Corporation, Madison, Wis.), MAXIscript® (Life Technologies, Grand Island, N.Y.), T7 High Yield RNA Synthesis Kit (New England Biolabs, Ipswich, Mass.), SP6/T7 Transcription Kit (Roche Applied Science, Indianapolis, Ind.), and the like.

In some instances, nucleic acids of the instant disclosure, e.g., nucleic acid templates, interfering nucleic acids (e.g., dsRNA), etc., and nucleic acid reagents including those synthetically or recombinantly produced, may be obtained from one or more commercial suppliers or commercial custom synthesis companies, including but not limited to e.g., IBA GmbH (Goettingen, Germany), Eurofins Genomics (Ebersberg, Germany), tebu-bio (Le Perray-en-Yvelines, France), Sigma-Aldrich (St Louis, Mo.), Ambion (Austin, Tex.), Applied Biosystems (Foster City, Calif.), Avecia OligoMedicines (Milford, Mass.), BioCat (Heidelberg, Germany), BioSpring (Frankfurt, Germany), Exiqon (Vedbaek, Denmark), GenScript (Piscataway, N.J.), Gene Tools (Philomath, Oreg.), Imgenex (San Diego, Calif.), Integrated DNA Technologies (Coralville, Iowa), Life Technologies (Grand Island, N.Y.), MWG-Biotech (Ebersberg, Germany), Oligoengine (Seattle, Wash.), QIAGEN (Germantown, Md.), SABiosciences (Frederick, Md.), Sigma-Genosys (The Woodlands, Tex.), and the like.

In certain embodiments of the present disclosure, dsRNA constructs may also be transformed into an organism, e.g., a phage, a virus, a prokaryote, a eukaryote, a bacterium, a yeast, a cell of a cell culture system, a cell of a mammalian cell culture system, a plant, a cell of a plant cell culture system, and the like, for the purpose of generating dsRNA in vivo. Methods for production of dsRNA in vivo, e.g., by introducing a dsRNA construct into a living cell by transformation of dsRNA constructs, are well known in the art, see, e.g., Timmons et al. (2001) *Gene,* 263:103-112; Newmark et al. (2003) *Proc Natl Acad Sci USA,* 100 Supp 1:11861-5; Reddien et al. (2005) *Developmental Cell,* 8:635-649; U.S. Pat. Nos. 6,506,559; and 7,282,564, the disclosures of which are incorporated herein by reference. In certain instances, the dsRNA construct comprises inducible promoters positioned to allow production of both sense and antisense RNA, e.g. different inducible promoters positioned on both sides of the introduced dsRNA template or the same inducible promoters positioned on both sides of the introduced dsRNA template. Inducible promoters are examples of transcriptional control elements and such transcriptional control elements, as detailed herein, find use in generating dsRNA are well known in the art.

Transcriptional control elements, e.g., promoters, and enhancers, etc. may be operably linked to a dsRNA template to control production of dsRNA either in vitro or in vivo. Such elements may be constitutively active or preferably controllable through the introduction of a stimulus, e.g., an environmental stimulus (e.g., change in temperature, pH, light exposure, and the like), a chemical or biological stimulus (e.g., a small molecule or chemical, a molecular biology reagent that binds to an activator or repressor, and the like). Transcriptional control elements may be bound to a dsRNA template singly or in arrays containing multiple transcriptional control elements, e.g., about 2, about 3, about 4, about 5, or more than 5 transcriptional control elements. In certain embodiments, transcriptional control elements are operably linked, directly or indirectly to both the 5' and the 3' ends a dsRNA template and such arrangements may place transcriptional control elements on either side of a dsRNA template such that the elements are arranged in a parallel or antiparallel manner.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Suitable inducible promoters, including reversible inducible promoters are known in the art. Such inducible promoters may be isolated and derived from many organisms, e.g., eukaryotes and prokaryotes. Modification of inducible promoters derived from a first organism for use in a second organism, e.g., a first prokaryote and a second a eukaryote, a first eukaryote and a second a prokaryote, etc., is well known in the art. Such inducible promoters, and systems based on such inducible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like. Certain aspects of the invention make use of plant inducible promoters, such as is well known in the art, e.g., see Borghi (2010) *Methods Mol Biol,* 655:65-75, the entirety of which is incorporated herein by reference.

In some instances, the locus or construct or transgene containing the suitable promoter is irreversibly switched through the rearrangement of elements of the construct or transgene, in certain instances by induction of an inducible system. Site-specific recombination may render a promoter irreversibly switched and such recombinations typically make use of cofactors, e.g., DNA-binding proteins, DNA-binding sites, site specific recombinases, and the like, that result in a change in the spatial arrangement of a elements, e.g., promoter elements or regulatory elements, and the dsRNA template. Such rearrangement of elements can be performed in eukaryotic cells, e.g., insect cells and plant cells, and prokaryotic cells, e.g., bacteria, and such methods are well known. Suitable systems for induction of an irreversible switch are well known in the art, e.g., induction of an irreversible switch may make use of a Cre-lox-mediated recombination (see, e.g., Fuhrmann-Benzakein, et al., *PNAS* (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. (2006) *Annual Review of Biochemistry,* 567-605 and Tropp (2012) Molecular Biology (Jones & Bartlett Publishers, Sudbury, Mass.), the disclosures of which are incorporated herein by reference.

In certain instances, following generation of dsRNA from a dsRNA construct, e.g., a plasmid, by an organism, e.g., a bacterium or an animal or a plant, the produced dsRNA may be isolated and/or purified according to any convenient method of RNA isolation and/or purification. Isolated and purified dsRNA may also be produced by in vitro methods already discussed. dsRNA, e.g., isolated and purified dsRNA, may be delivered to a target or host organism, e.g., a Hymenoptera host, e.g., an ant host, e.g., an Argentine ant host, e.g., *Linepithema humile,* unprocessed or without processing of the dsRNA, i.e., dsRNA processing, by any convenient method of introducing the dsRNA described herein or known in the art. In certain instances, dsRNA is processed, e.g., subjected to dsRNA processing or dsRNA in vitro processing, before being introduced into a target or host organism. As used herein, by "dsRNA processing" is meant subjecting a dsRNA to one or more physical forces, one or more chemicals, or one or more enzymes or a combination thereof in order to cleave or digest the dsRNA. Non-limiting examples of enzymes that find use in dsRNA processing include, e.g., a nuclease, a ribonuclease, a RNase, a restriction enzyme, a component of an RNAi processing pathway, e.g., RNase III, Dicer, Drosha, and the like. The skilled artisan will recognize that any convenient method of processing dsRNA may be utilized to generate siRNA as such methods are well known in the art and described below.

In some embodiments, siRNA is produced by methods not requiring the production of dsRNA, e.g., chemical synthesis or de novo synthesis or direct synthesis. Chemically synthesized siRNA may be synthesized on a custom basis or may be synthesized on a non-custom or stock or pre-designed basis. Custom designed siRNA are routinely available from various manufactures (e.g., Ambion®, a division of Life Technologies®, Grand Island, N.Y.; Thermo Scientific®, a division of Fisher Scientific®, Pittsburgh, Pa.; Sigma-Aldrich®, St. Louis, Mo.; Qiagen®, Hilden, Germany; etc.) which provide access to various tools for the design of siRNA. Tools for the design of siRNA allow for the selection of one or more siRNA nucleotide sequences based on computational programs that apply algorithms on longer input nucleotide sequences to identify candidate siRNA sequences likely to be effective in producing an RNAi effect. Such algorithms can be fully automated or semi-automated, e.g., allowing for user input to guide siRNA selection. Programs applying algorithms for siRNA sequence selection are available remotely on the World Wide Web, e.g., at the websites of manufacturers of chemically synthesized siRNA or at the websites of independent, e.g. open source, developers or at the websites of academic institutions. Programs applying algorithms for siRNA sequence selection may also be obtained, e.g., downloaded or received on compact disk as software. Such programs are well known in the art, see e.g., Naito et al. (2004) *Nucleic Acids Research,* 32:W124-W129; Boudreau et al. (2013) *Nucleic Acids Research,* 41:e9; Mysara et al. (2011) *PLoS,* 6:e25642; and Iyer et al. (2007) *Comput Methods Programs Biomed,* 85:203-9, which are incorporated herein by reference.

Publicly available tools to facilitate design of siRNAs are available in the art. See, e.g., DEQOR: Design and Quality Control of RNAi (available on the internet at http://deqor(dot)mpi-cbg(dot)de/deqornew/input(dot)html). See also, Henschel et al. Nucleic Acids Res. 2004 Jul. 1; 32(Web Server issue):W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

The terms "short interfering nucleic acid," "siNA," "short interfering RNA," "siRNA," "short interfering nucleic acid molecule," "short interfering oligonucleotide molecule," and "chemically-modified short interfering nucleic acid molecule" as used herein refer to any nucleic acid molecule capable of inhibiting or down regulating gene expression, for example by mediating RNA interference "RNAi" or gene silencing in a sequence-specific manner Design of RNAi molecules, when given a target gene, is routine in the art. See also US 2005/0282188 (which is incorporated herein by reference) as well as references cited therein. See, e.g., Pushparaj et al. *Clin Exp Pharmacol Physiol.* 2006 33(5-6): 504-10; Lutzelberger et al. *Handb Exp Pharmacol.* 2006 (173):243-59; Aronin et al. *Gene Ther.* 2006 13(6):509-16; Xie et al. *Drug Discov Today.* 2006 11(1-2):67-73; Grunweller et al. *Curr Med Chem.* 2005 12(26):3143-61; and Pekaraik et al. *Brain Res Bull.* 2005 68(1-2):115-20, the disclosures of which are incorporated herein by reference in their entirety.

Methods for design and production of siRNAs to a desired target are known in the art, and their application to elongase and cuticular hydrocarbon genes for the purposes disclosed herein will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US2002/0120129, each of which are incorporated herein by reference.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, *Cell.*, 110, 563-574 and Schwarz et al., 2002, *Molecular Cell,* 10, 537-568, the disclosures of which are incorporated herein by reference in their entirety), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. siNAs do not necessarily require the presence of nucleotides having a 2'-hydroxy group for mediating RNAi and as such, siNA molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In some embodiments, an siNA is an siRNA. In some embodiments, a DNA comprising a nucleotide sequence encoding an siRNA is used. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence a target gene at the post-transcriptional level or the pre-transcriptional level. In a non-limiting example, epigenetic regulation of gene expression by siNA molecules of the invention can result from siNA mediated modification of chromatin structure or methylation pattern to alter gene expression (see, for example, Verdel et al., 2004, *Science*, 303, 672-676; Pal-Bhadra et al., 2004, *Science*, 303, 669-672; Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237, the disclosures of which are incorporated by reference herein in their entirety).

siNA (e.g., siRNA) molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178).

siNA (e.g., siRNA) molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 *Nature* 344, 565; Pieken et al., 1991, *Science* 253, 314; Usman and Cedergren, 1992, *Trends in Biochem. Sci.* 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334, 711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Eamshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; each of which are hereby incorporated in their totality by reference herein). In view of such teachings, similar modifications can be used as described herein to modify the siNA nucleic acid molecules of disclosed herein so long as the ability of siNA to promote RNAi is cells is not significantly inhibited.

Short interfering nucleic acid (siNA) molecules (e.g., siRNA) having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, *Nucleic Acids Res.* 23, 2677; Caruthers et al., 1992, *Methods in Enzymology* 211, 3-19, incorporated by reference herein). In one embodiment, nucleic acid molecules of the invention include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, *J. Am. Chem. Soc.*, 120, 8531-8532, incorporated by reference herein). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes includes those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine) In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

Nucleic Acid Modifications

In some embodiments, a subject nucleic acid (e.g., a dsRNA, a siNA, etc.) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid (e.g., a dsRNA, a siNA, etc.) has one or more nucleotides that are 2'-O-Methyl modified nucleotides. In some embodiments, a subject nucleic acid (e.g., a dsRNA, a siNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a dsRNA, a siNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, *Biochemistry*, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH$_2$—), group bridging the 2' oxygen atom and the 4' carbon atom wherein n is 1 or 2 (Singh et al., *Chem. Commun.*, 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.*, 2000, 97, 5633-5638, the disclosure of which is incorporated herein by reference in its entirety).

The synthesis and preparation of the LNA monomers adenine, cytosine, guanine, 5-methylcytosine, thymine and uracil, along with their oligomerization, and nucleic acid recognition properties have been described (e.g., Koshkin et al., *Tetrahedron*, 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O—, S—, or N-alkyl; O—, S—, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—O $CH_2CH_2CH_2NH_2$), allyl (—$CH_2$—CH=$CH_2$), —O-allyl $CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering,* pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, *Antisense Research and Applications,* pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., *Antisense Research and Applications,* CRC Press, Boca Raton, 1993, pp. 276-278; the disclosure of which is incorporated herein by reference in its entirety) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the 3' terminus of an exogenous polynucleotide (e.g., a dsRNA or siNA). In some embodiments, a PTD is covalently linked to the 5' terminus of an exogenous polynucleotide (e.g., a dsRNA or siNA). Exemplary PTDs include but are not limited to a minimal undecapeptide protein transduction domain (corresponding to residues 47-57 of HIV-1 TAT comprising YGRKKRRQRRR; SEQ ID NO:19); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila Antennapedia* protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci.* USA 97:13003-13008); RRQRRTSKLMKR SEQ ID NO:20); Transportan GWTLNSAGYLLGKINLKALAALAKKIL SEQ ID NO:21); KALAWEAKLAKALAKALAKHLAKALAKALKCEA SEQ ID NO:22); and RQIKIWFQNRRMKWKK SEQ ID NO:23). Exemplary PTDs include but are not limited to, YGRKKRRQRRR SEQ ID NO:24), RKKRRQRRR SEQ ID NO:25); an arginine homopolymer of from 3 arginine residues to 50 arginine residues; Exemplary PTD domain amino acid sequences include, but are not limited to, any of the following: YGRKKRRQRRR SEQ ID NO:26); RKKRRQRR SEQ ID NO:27); YARAAARQARA SEQ ID NO:28); THRLPRRRRRR SEQ ID NO:29); and GGRRARRRRRR SEQ ID NO:30). In some embodiments, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Target Genes

Reduction of gene expression (e.g., transcription and/or translation) of a target gene of interest results in a reduction of the viability and/or activity of a host organism in which the target gene is present. In certain embodiments, target genes are those genes which are uniquely present in a particular group of targeted host organisms, e.g., genes uniquely present in arthropods, gene uniquely present in Chelicerata, genes uniquely present in Myriapodia, genes uniquely present in Hexipodia, genes uniquely present in Arachnida, genes uniquely present in Insecta, genes uniquely present in Archaeognatha, genes uniquely present in Thysanura, genes uniquely present in Palaeoptera, genes uniquely present in Ephemeroptera, genes uniquely present in Odonata, genes uniquely present in Anisoptera, genes uniquely present in Zygoptera, genes uniquely present in Neoptera, genes uniquely present in Exopteiygota, genes uniquely present in Plecoptera, genes uniquely present in Embioptera, genes uniquely present in Orthoptera, genes uniquely present in Zoraptera, genes uniquely present in Dermaptera, genes uniquely present in Dictyoptera, genes uniquely present in Notoptera, genes uniquely present in Giylloblattidae, genes uniquely present in Mantophasmatidae, genes uniquely present in Phasmatodea, genes uniquely present in *Blattaria*, genes uniquely present in Isoptera, genes uniquely present in Mantodea, genes uniquely present in Parapneuroptera, genes uniquely present in Psocoptera, genes uniquely present in Thysanoptera, genes uniquely present in Phthiraptera, genes uniquely present in Hemiptera, genes uniquely present in Endopteiygota or Holometabola, genes uniquely present in Hymenoptera, genes uniquely present in Coleoptera, genes uniquely present in Strepsiptera, genes uniquely present in Raphidioptera, genes uniquely present in Megaloptera, genes uniquely present in Neuroptera, genes uniquely present in Mecoptera, genes uniquely present in Siphonaptera, genes uniquely present in Diptera, genes uniquely present in Trichoptera, or genes uniquely present in Lepidoptera.

Target genes of interest in connection with the present disclosure include target genes uniquely present in sub-orders, families, sub-families, groups, sub-groups, or species of Hymenoptera. For example, target genes of interest in connection with the present disclosure include genes uniquely present in ants, genes uniquely present in wasps, genes uniquely present in bees, genes uniquely present in sawflies, or genes uniquely present in horntails.

Target genes of interest in connection with the present disclosure, and gene or gene families uniquely present in particular groups of organisms, may be identified by any convenient method. Identification of target genes may be performed by searching publicly available electronic databases of nucleotide sequences or genomic databases. For example, target genes may be identified by searching publicly available databases hosted by the NCBI (at www(dot)ncbi(dot)nlm(dot)nih.gov) such as, e.g., the *Acyrthosiphon pisum* (pea aphid) database, the *Aedes aegypti* (yellow fever mosquito) database, the *Anopheles gambiae* (African malaria mosquito) database, the *Apis mellifera* (honey bee) database, the *Bombus terrestris* (buff-tailed bumblebee) database, the *Drosophila melanogaster* (fruit fly) database, the *Drosophila pseudoobscura* (fruit fly) database, the *Drosophila virilis* (fruit fly) database, the *Nasonia vitripennis* (jewel wasp) database, or the *Tribolium castaneum* (red flour beetle) database. Target genes may also be identified by searching publicly available databases provided by The Hymenoptera Genome Database (HGD) Project (hymenopteragenome(dot)org) such as, e.g., bee genome databases of *Apis mellifera*, *Bombus terrestris* and *B. impatiens*; the wasp genome database of *Nasonia vitripennis*, the ant genome databases of the fungus eating ant *Acromyrmex echinatior*, the leaf cutter ant *Atta cephalotes*, the Florida Carpenter ant *Camponotus floridanus*, Jerdon's Jumping ant *Harpegnathos saltator*, the Argentine ant *Linepithema humile*, the red harvester ant *Pogonomyrmex barbatus* and the fire ant *Solenopsis invicta*. Those skilled in the art will readily understand the identification of target genes is not limited to genes or nucleotide sequences contained in genomic databases for those organisms for which genomic databases are publicly available. Methods for isolation and identifying genes, e.g., target genes, in organisms lacking databases of genomic information, either de novo or by comparison to a related organism for which genomic information is available, are well known in the art, see, e.g., Green & Sambrook (2012) *Molecular Cloning: A Laboratory Manual* (Fourth Edition) Cold Spring Harbor, N.Y.: Cold Spring Harbor Press; Brown (2013) *Next-Generation DNA Sequencing Informatics*. Cold Spring Harbor, N.Y.: Cold Spring Harbor Press; and Birren et al. (1999) *Genome Analysis: A Laboratory Manual* (Vol. 3, Cloning Systems) Cold Spring Harbor, N.Y.: Cold Spring Harbor Press, the disclosures of which are incorporated herein by reference.

According to certain embodiments of the present disclosure, target genes may include those genes necessary for insect, e.g., ant, normal physiological processes or metabolic processes. For example, target genes may include those genes involved in insect energy storage or energy release, e.g., fat metabolism, carbohydrate metabolism, and protein metabolism, see, e.g., Arrese & Soulages (2010) *Annual Reviews Entomology*, 55:207-25; and Kunieda et al. (2006) *Insect Mol Biol*, 15:563-76, which are incorporated by reference herein. According to certain embodiments of the present disclosure, target genes may be identified using the Argentine ant genome assembly, see, e.g., Smith et al. (2010) *Proc Natl Acad Sci*, 108:5673-8, the disclosure of which is incorporated by reference herein.

According to certain embodiments of the present disclosure, target genes may include those genes necessary for insect, e.g., ant, production of chemicals necessary for nestmate recognition, e.g., cuticular hydrocarbons (CHCs), odorant receptors, etc. Any gene involved in the metabolism of CHCs or CHC precursors or in the synthesis and production of CHCs find use as target genes of the present disclosure, see e.g., Blomquist, & Bagnères (2010) *Insect Hydrocarbons: Biology, Biochemistry, and Chemical Ecology*. New York: Cambridge University Press and Howard, R. W., and Blomquist (2005) *Annu Rev Entomol*, 50:371-393, the disclosures of which are incorporated by reference herein. In certain embodiments of the present disclosure, targeted genes affecting CHC synthesis and production are genes acting on metabolites to form CHC compounds, e.g., desaturases, elongases, and decarboxylases. In certain instances, desaturases, the gene products of desaturase genes, and related proteins act to transform palmitic acid to palmitoleic acids, stearic acids to oleic acids, and myristic acid to myristoleic acid in order to produce or modify CHCs necessary for insect communication, e.g., nestmate recognition or mate recognition. In certain instances, elongases, the gene products of elongase genes, extend the carbon chains of precursor CHCs allowing the production of fully processed CHCs necessary for insect communication. One skilled in the art will readily recognize, based on the present knowledge in the art of CHC synthesis and production, other genes that can be targeted to affect CHC production, insect communication, as well as insect and colony viability.

In some cases, a target gene is an elongase gene. For example, in some cases, a target gene comprises a nucleotide sequence having at least 75%, at least 80%, at least 85%, at least 90%, at least 95%, at least 98%, at least 99%, or 100%, nucleotide sequence identity with any one of the elongase sequences depicted in FIG. 1.

In some cases, a target gene is a desaturase gene. For example, in some cases, a target gene comprises a nucleotide sequence having at least 75%, at least 80%, at least 85%, at least 90%, at least 95%, at least 98%, at least 99%, or 100%, nucleotide sequence identity with a desaturase nucleotide sequence set out in GenBank EH413189.1, where the nucleotide sequence set out in GenBank EH413189.1 is:

```
                                    (SEQ ID NO: 31)
AAGTGACGCACACTACCAGAATTCTGTTAACAGATTTTACACAACAATGG

CGCCGAATATAACAATTAAATCAACAGGAGTACTATTCGAAGATGAGACT

CTTGGCGAACCGCAAGTAGTTGAAGAGCTGAAGGATAAATCTAAATATGT

TAGGCGCATTGAGTGGAAAAGAGTAATATTTTTCTCGTTTCTACATCTCG

GTGCCCTTTTCGGCGTTTATCTTTTATTCACATCTGTCAAATTTGCTACC

ATTTTATTTGTAATTTTCTTATCTGAAATCAGCTTGATGGGAATCACAGC

TGGAAATCATCGACTGTGGGCACACCGATCTTATAAAGCCAAGTGGCCTC

TCCAGCTGCTGCTTGTTATTATGAGCACTATAGCGTTTCAGTTCGATGTG

ATCCATTGGTCCAGAGATCATAGGGTTCACCACAAATACAGTGAAACTGA

CGCCGATCCGCATAATGCTAAAAGAGGTTTCTTCTTCGCACATGTGGGCT

GGCTGGTTTGCAGGAAACATTCAGAAGTCAAGAAAAAAGGCAAAGAAATT

GACATAAGCGATCTTGAAAGCAATCCAATATTAGCATTCCAAAAGAAATA

TTATNAACATACTGGTGCTATTGCTCTGCTTTATTTTACCAACCGTC.
```

In some instances, a target gene is a desaturase gene identified as a desaturase gene or gene fragment in the *Linepithema humile* Genome (available at http(colon)//hymenopteragenome(dot)org). Identified desaturase genes and gene fragments include, e.g., Lhum_CG9747_a, Lhum_CG9747_b, Lhum_CG9747_c, Lhum_CG9747_d, Lhum_CG9747_e, Lhum_CG9747_f, Lhum_CG9747_g, Lhum_CG9747_h, Lhum_CG9747_i, Lhum_CG9747_j, Lhum_CG9747_k, Lhum_CG9747_1, Lhum_CG9747_m, Lhum_CG9747_n, Lhum_CG9747_o, Lhum_CG9747_p, Lhum_desat_frag1, Lhum_desat_frag7, Lhum_desat_frag8, Lhum_desat_frag9, Lhum_CG8630_a, Lhum_CG8630_b, Lhum_CG8630_c, Lhum_CG8630_d, Lhum_CG9743, Lhum_CG15531, Lhum_desat_frag2, Lhum_desat_frag3, Lhum_desat_frag4, Lhum_desat_frag5, Lhum_desat_frag6, Lhum_desat1_a, Lhum_desat1_b, and those mRNA transcripts, CDS, and exons thereof.

In some instances, a target gene is an elongase gene, e.g., an elongase gene or gene fragment in the *Linepithema humile* Genome (available at http(colon)//hymenopteragenome(dot)org) which may be identified through bioinformatics (e.g., by homology searches). In some instances, an elongase target gene is an elongase gene identified in the instant disclosure including but not limited to, e.g., LH16891, LH23306, LH17398, LH11439b, LH18968, LH11831, and the like; the sequences of which, including CDS sequences, exon sequences, and associated gene locus sequence, which may or may not be specifically provided herein, may be retrieved from the *Linepithema humile* Genome (available at http(colon)//hymenopteragenome(dot) org.

In some instances, a target gene is a decarboxylase gene, e.g., a decarboxylase gene or gene fragment in the *Linepithema humile* Genome (available at http(colon)//hymenopteragenome(dot)org) which may be identified through bioinformatics (e.g., by homology searches).

Formulations

The present disclosure provides formulations comprising an RNAi, e.g., formulations comprising a dsRNA, formulations comprising an siNA, or formulations comprising an organism containing dsRNA or siNA, e.g., transformed bacteria containing dsRNA. Formulations of the present disclosure include formulations suitable for various modes of delivery of interfering nucleic acids described herein. Formulations of the present disclosure include any formulation that provides for the delivery of an effective amount of interfering nucleic acid to a target host organism, such that, the formulation maintains or enhances the desired effect, e.g., decreasing the viability and/or activity of a host organism, of a interfering nucleic acid. Formulations that maintain the desired effect of an interfering nucleic acid include formulations that preserve, e.g., formulations containing a preservative agent, an interfering nucleic acid or formulations that do not disrupt or decrease the activity of an interfering nucleic acid but also provide some other enhancement or benefit. Such enhancements or benefits, e.g., formulations that enhance the desired effect of an interfering nucleic acid, include, but are not limited to, enhanced dispersal of an interfering nucleic acid to increase the chance of interaction between an interfering nucleic acid and a target host organism or enhanced delivery of an effective amount of an interfering nucleic acid to or into a target host organism. In certain embodiments, formulations also contain agents that enhance the desired effect, e.g., decreased viability and/or activity of the target host organism, of the interfering nucleic acid. Such agents include, but are not limited to, chemical agents that further inhibit a biological pathway or metabolic pathway to which the interfering nucleic acid is targeted or chemical agents that inhibit a related biological pathway or metabolic pathway to which the interfering nucleic acid is targeted. In some embodiments, formulations include agents, e.g., chemical agents or toxic agents that generally affect viability of the target host organism, e.g., toxicants or pesticides or insecticides. Encompassed herein are formulations that contain combinations of one or more additional agents, i.e., an agent in addition to the interfering nucleic acid present in the formulation, e.g., formulations with one additional agent, formulations with two additional agents, formulations with three additional agents, formulations with four additional agents, formulations with five additional agents, formulations with six additional agents, or formulations with more than six additional agents.

This invention further provides spray compositions for controlling an invertebrate pest comprising a subject interfering nucleic acid or a composition comprising a subject interfering nucleic acid (i.e. in a biologically effective amount), and a propellant. This invention also provides a bait composition for controlling an invertebrate pest comprising a subject interfering nucleic acid, one or more food materials, optionally an attractant, and optionally a humectant.

Pesticide and insecticide formulations, e.g., bait formulations and spray formulations and the like are well known in the art, see, e.g., U.S. Patent Application Publication Nos. 2013/0,217,574; 2013/0,195,946; 2013/0,149,278; 2012/0,148,653; 2011/0,262,382; 2011/0,258,908; 2011/0,236,451; 2011/0,200,551; 2011/0,046,124; 2010/0,247,480; 2010/0,192,452; 2010/0,074,860; 2010/0,031,556; 2009/0,148,398; 2007/0,122,442; 2007/0,014,825; 2006/0,270,737; 2005/0,244,446; 2005/0,209,344; 2004/0,057,976; 2003/0,207,806; 2003/0,054,391, 2013/0,288,897 and 2013/0,252,960 the disclosures of which are incorporated by reference herein.

Spray formulations of the present disclosure include the active agents (i.e. an interfering nucleic acid) and a suitable propellant, e.g., n-butane, wherein a suitable propellant is any propellant that does not negatively affect the stability or functionality of the active agent(s). In certain embodiments, the active agent is dissolved in or dispersed in a suitable medium, such as water or buffer or water miscible liquid, e.g., n-propanol, ethanol, etc. Spray formulations of the present disclosure may be pressurized or non-pressurized. Pressurized spray formulations may contain a gas, e.g., an inert gas, e.g., nitrogen gas, or any gas that does not negatively affect the stability or functionality of the active agent. Non-pressurized formulations may be contained in a manually pressurized container, e.g., hand-actuated spray pumps or mechanically activated spray pumps. In some instances, the propellant is a propellant other than nitrogen, e.g., n-propane, n-butane, iso-pentane, iso-butane, n-pentane, hydrofluorocarbons, and the like.

Bait containing compositions of the present disclosure may be solid or semi-solid or liquid formulations. Any suitable bait may find use in the present disclosure, and represents any natural or synthetic agent, e.g., chemical, biochemical, foodstuff, added to the formulation to enhance feeding or serve as a feeding stimulant, e.g., a phagostimulant. Natural bait agents may include natural sources of food for the target organisms in the wild. Natural bait agents may also include foodstuffs or food production byproducts or purified food components or ingredients that the target organism would not normally be exposed to in the wild. Exemplary naturally occurring feeding stimulants for insects include, but are not limited to, cellulosic baits, sitosterol, food oils, vegetable oil, corn oil, peanut oil, egg yolk, sugar, sucrose, fructose, glucose, maltose, trehalose, honey, cane syrup and molasses. In some embodiments, foodstuff based baits include one or more additional ingredients or a combination of different foodstuffs, e.g., oils and sugars, sugars and amino acids, sugars and proteins, etc amino acids that find use as bait additives include alanine, asparagine, aspartic acid, glutamic acid, glutamine, glycine, histidine, phenylalanine, proline, serine, threonine, and valine. Bait formulations may also include preservatives, e.g., sodium benzoate, citric acid, or a mixture of sodium benzoate and citric acid, to prevent decomposition of the bait during use or storage. In some embodiments, bait compositions are combined with spray formulations to produce a bait spray formulation.

Formulations of the present disclosure include those formulations comprising or in the form of nectar or honeydew. Any convenient source of nectar or honeydew, whether natural or synthetic, may find use in the compositions, formulations, or methods of the present disclosure. Nectar may be derived from natural sources, e.g., a tree, a shrub, a flower, a fruit, a crop, an herb, a grass, and the like, that are a wild source of nectar for the target host organism. In certain embodiments, nectar is derived from natural sources, e.g., a tree, a shrub, a flower, a fruit, a crop, an herb, a grass, and the like, that are not a wild source of nectar for the target host organism. In some embodiments, nectar is produced, e.g., made synthetically, through dissolving one or more sugars, e.g., sucrose, fructose, glucose, maltose, etc. with water. In certain instances, nectar consists only of water and sugar. In some embodiments, nectar contains additional components, e.g., oils, amino acids, and the like.

In certain embodiments, convenient sources of honeydew find use in the compositions, formulations, or methods of the present disclosure. Honeydew of the present disclosure typically contains less sugar, i.e., lower sugar concentration, than nectar. Synthetic honeydew that finds use in compositions of the present disclosure may be formulated to resemble naturally occurring honeydew, e.g., honeydew excreted by aphids. Synthetic honeydew that finds use in compositions of the present disclosure may be supplemented with additional components not normally present in naturally occurring honeydew. Methods mimicking naturally occurring nectar and honeydew and compositions of synthetic nectar and honeydew are well known in the art, see, e.g., U.S. Pat. No. 7,048,918, the disclosure of which is incorporated herein by reference.

In some embodiments, isolated interfering nucleic acid is re-suspended or dissolved directly in nectar or honeydew. In certain embodiments, nectar or honeydew are combined with interfering nucleic acid of the present disclosure in a specific ratio, e.g., about 1:1 v/v interfering nucleic acid to nectar or honeydew, about 2:1 v/v interfering nucleic acid to nectar or honeydew, about 3:1 v/v interfering nucleic acid to nectar or honeydew, about 4:1 v/v interfering nucleic acid to nectar or honeydew, about 5:1 v/v interfering nucleic acid to nectar or honeydew, about 10:1 v/v interfering nucleic acid to nectar or honeydew, about 100:1 v/v interfering nucleic acid to nectar or honeydew, about 1:2 v/v interfering nucleic acid to nectar or honeydew, about 1:3 v/v interfering nucleic acid to nectar or honeydew, about 1:4 v/v interfering nucleic acid to nectar or honeydew, about 1:5 v/v interfering nucleic acid to nectar or honeydew, about 1:10 v/v interfering nucleic acid to nectar or honeydew, about 1:100 v/v interfering nucleic acid to nectar or honeydew. In certain instances, nectar or honeydew are mixed with organisms transformed to produce interfering nucleic acid as discussed herein, e.g., bacteria transformed to produce dsRNA. According to certain embodiments, a pellet of bacteria containing interfering nucleic acid is re-suspended in nectar or honeydew. In certain instances, a pellet of bacteria containing interfering nucleic acid is re-suspended in a suitable liquid for resuspension, e.g., water, media, or buffer, and nectar or honeydew is added to an effective concentration. In some embodiments, natural nectar is combined with synthetic honeydew. In some embodiments, synthetic nectar is combined with synthetic honeydew. In yet other embodiments, synthetic nectar is combined with natural honeydew.

Methods of Controlling Pests

The present disclosure provides methods of controlling pests through the introduction into the pest of an effective amount of an interfering nucleic acid as described herein. Methods of the present disclosure include the delivery of interfering nucleic acids designed to reduce the viability of a Hymenoptera host, e.g., an ant. Methods of the present disclosure include the delivery of interfering nucleic acids designed to reduce the activity of a Hymenoptera host, e.g., an ant. Methods of the present disclosure include the delivery of interfering nucleic acids designed to reduce the viability and the activity of a Hymenoptera host, e.g., an ant. Methods of the present disclosure make use of compositions and formulations described herein.

A subject method of controlling a pest generally involves introducing into the pest an effective amount of an interfering nucleic acid as described herein. In some cases, an "effective amount" of an interfering nucleic acid is an amount that, when introduced into a host, reduces the level of a target gene product (an RNA or polypeptide product of a target gene) by at least about 10%, at least about 15%, at least about 20%, at least about 25%, at least about 30%, at least about 40%, at least about 50%, or more than 50%, compared to the level of the target gene product in the host not treated with the interfering nucleic acid.

In some cases, an "effective amount" of an interfering nucleic acid is an amount that, when introduced into a host, reduces the viability of the host. For example, in some embodiments, an "effective amount" of an interfering nucleic acid is an amount that, when introduced into a host, reduces the viability of the host such that at least about 10%, at least about 15%, at least about 20%, at least about 25%, at least about 30%, at least about 40%, at least about 50%, at least about 60%, at least about 70%, at least about 80%, at least about 90%, or more than 90% of the host organisms in a population of the host organisms have reduced viability. For example, in some cases, an "effective amount" of an interfering nucleic acid is an amount that, when introduced into a population of host organisms, results in death of at least about 10%, at least about 15%, at least about 20%, at least about 25%, at least about 30%, at least about 40%, at least about 50%, at least about 60%, at least about 70%, at least about 80%, at least about 90%, or more than 90% of the host organisms, compared to a population of the host organisms not treated with the interfering nucleic acid.

In some cases, an "effective amount" of an interfering nucleic acid is an amount that, when introduced into a host, reduces an activity or a characteristic of the host. For example, in some embodiments, an "effective amount" of an interfering nucleic acid is an amount that, when introduced into a host, reduces an activity or a characteristic of the host by at least about 10%, at least about 15%, at least about 20%, at least about 25%, at least about 30%, at least about 40%, at least about 50%, at least about 60%, at least about 70%, at least about 80%, at least about 90%, or more than 90%, compared to the level of the activity or characteristic in the host not treated with the interfering nucleic acid. Activities and characteristics include but are not limited to nestmate recognition, queen recognition, larvae recognition, egg recognition, desiccation resistance, and microbial resistance.

A subject composition, suitable for use in a subject method, can be used to control Hymenoptera (ants, wasps, and bees). A non-exhaustive list of these pests includes, but is not limited to, *Acromyrrmex* spp., *Athalia rosae*, *Atta* spp. (leafcutting ants), *Camponotus* spp. (carpenter ants), *Diprion* spp. (sawflies), *Formica* spp. (ants), *Linepithema humile* (Argentine ant, formally *Iridomyrmex humilis*), *Monomorium* ssp., *Monomorium minumum* (little black ant), *Monomorium pharaonic* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees), and the like.

A subject composition suitable for use in a method of the present disclosure comprises an interfering nucleic acid for reducing the expression or activity of a target gene described herein. In some embodiments, the Hymenoptera pest targeted for control by a composition of the present disclosure is the same Hymenoptera species from which the target gene sequence encoding the interfering nucleic acid is derived. Alternatively, the Hymenoptera pest targeted for control by a composition of the present disclosure may be a different Hymenoptera species from which the target gene sequence encoding the interfering nucleic acid is derived. As such, one skilled in the art will recognize that any Hymenoptera species having a gene with sufficient similarity, i.e., sufficient to produce an RNAi effect, to the sequence from which a particular interfering nucleic acid was derived, e.g., a homologous gene to a target gene or an orthologous gene to a target gene, may be targeted with a composition containing the interfering nucleic acid.

Methods of controlling pests using compositions of the present disclosure include methods of using bait, e.g., compositions comprising bait as disclosed herein. Such methods may be utilized to incrementally increase the concentration of interfering nucleic acid in a target host organism or within a population of target host organisms in order to reach an effective amount of an interfering nucleic acid. For example, bait may be utilized such that a target host organism feeds on a subject composition multiple times thus incrementally increasing the amount of interfering nucleic acid delivered to the target host organism with each feeding. According to the present disclosure, bait is also employed to deliver the interfering nucleic acid to further individuals of a target host organism population, e.g., further individuals of a target host organism colony, e.g., further individuals of an ant colony. One skilled in the art will recognize the utility of such uses of bait and the variety of methods employing bait that may be used in the subject invention to increase the exposure of individuals, groups and communities of target host organisms to compositions including the interfering nucleic acid. In certain embodiments, a method of the present disclosure also involves the use of combinations of baits, e.g., two or more baits, e.g., three or more baits, e.g., four or more baits, e.g., more than five baits, in a subject composition or formulation.

In certain embodiments, methods of the present disclosure are directed at using interfering nucleic acids to reduce the viability and/or activity of pests by disrupting or inhibiting normal pest behaviors. In certain instances, the targeted pest behaviors are insect behaviors, e.g., insect social behaviors. Such targeted insect social behaviors include, but are not limited to, nestmate recognition, queen recognition, larvae recognition, egg recognition, and the like. Such targeted insect social behaviors include, but are not limited to, ant nestmate recognition, queen ant recognition, ant larvae recognition, ant egg recognition, and the like. In certain instances, the targeted pest behaviors are normal insect physiological functions. Such targeted insect physiological functions include, but are not limited to, desiccation resistance, microbial resistance, and the like. For example, such targeted insect physiological functions include, but are not limited to, ant desiccation resistance, ant microbial resistance, and the like.

One skilled in the art will recognize, as insect behaviors are well understood, that any insect behavior that ultimately affects insect viability and/or activity may be targeted in methods of the present invention. One skilled in the art will also recognize that insect behaviors, e.g., ant behaviors, that may be targeted in methods of the subject invention include those behaviors that, while not directly deleterious to the initial ant in which RNAi is triggered, may be subsequently deleterious to the colony to which the ant belongs.

Methods of controlling pests using compositions of the present disclosure include methods of using plants genetically modified to produce interfering nucleic acids as described herein. Genetically modified plants may stably or transiently produce or express interfering nucleic acids of the subject disclosure. Any convenient means of stable and/or transient transformation of plants with one or more subject interfering nucleic acids may be used including but not limited to, e.g., biolistics (e.g., gene gun), electroporation, coprecipitation-based transfer, *Agrobacterium*-mediated DNA transfer, virus-based gene transfer, micromanipulation, and the like. Following introduction of the subject nucleic acid, the introduced construct (e.g., dsRNA template, siNA template, etc.) may integrate into the plant genome, e.g., through the use of any convenient genomic integration method (e.g., homologous recombination, targeted integration, etc.) or may remain extrachromosomal or extranuclear. Genomic integrated subject nucleic acids may make use of construct supplied control elements (e.g., promoters) or may make use of host control elements (e.g., native host promoters at the integration site) or both. Non-integrating constructs will generally rely on introduced control elements, e.g., control elements (e.g., promoters) that have been introduced with the subject nucleic acids. Methods of generating, analyzing and using transgenic plants are described in, e.g., *Transgenic Crop Plants: Volume 1: Principles and Development* (2010) Springer Science & Business Media: Ed. Kole C., et al., the disclosure of which is incorporated herein by reference in its entirety.

The methods of controlling pests as described herein find use in any plant subject to detrimental effects from pest infestation, including monocotyledons and dicotyledons. In some instances, plants of the instant disclosure include those plants affected by one or more sap-sucking or sap-feeding insect including but not limited to, e.g., aphids (e.g., Blue-green aphid, Cabbage aphid, Corn aphid, Cotton aphid, Cowpea aphid, Green peach aphid, Oat aphid, wheat aphid, Pea aphid, Rice root aphid, Rose-grain aphid, Soybean aphid, Spotted alfalfa aphid, Turnip aphid, etc.), whitefly, leafhopper (e.g., potato leafhopper), soft scale, scale, mealybugs, mites, true bugs (Hemiptera), harlequin bug, eggplant lace bug, squash bug, tarnished plant bug, some fly larvae, and the like. In some instances, the methods described herein may be directed to the control of insects that promote the survival and/or growth crop-destroying insects, e.g., sap-sucking or sap-feeding insects. In some instances, such insects that promote the survival and/or growth crop-destroying insects may be referred to as tending insects. In some instances, inhibiting or reducing the expression of one or more genes expressed by a tending insect as described herein may serve to control a crop-destroying insect or a sap-sucking or sap-feeding insect. Inhibition of one or more genes expressed by a tending insect may have a variety of outcomes that results in an adverse condition for a crop-destroying insect or a sap-sucking or sap-feeding insect including but not limited to, e.g., reduction of tending behaviors of the tending insect, reduced viability of the tending insect, reduced viability of a population of tending insects, reduced numbers of the tending insect, reduced numbers of populations of the tending insect, etc. In some embodiments, the tending insect may be an Argentine ant and a crop-destroying pest may include but is not limited to, e.g., an aphid, a scale insect, etc.

In some instances, plants of the instant disclosure, e.g., that may be treated with the nucleic acids described herein or may be genetically modified to produce the nucleic acids as described herein, are major agricultural crops which include but are not limited to, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like.

In some instances, plants of the instant disclosure, e.g., that may be treated with the nucleic acids described herein or may be genetically modified to produce the nucleic acids as described herein, are fruit crops which include but are not limited to, e.g., apples, apricots, avocados, bananas, batatas, bitter orange, black currants, blackberries, blood orange, blueberries, boysenberries, breadfruit, cactus pears, cantaloups, cape gooseberries (physalis), carambola (star fruit), casaba, charantais melon, cherimoya, cherries, citron, clementines, cocktail grapefruit/pummelo, coconuts, cranberries, crenshaw, dates, dragon fruit (red pitaya), durian, edible flowers, feijoa, figs, galia melon, gaya melon, gooseberries, grapefruit, grapes, guava, hami melon, homelyfruit, honeydews, jackfruit, juan canary melon, jujube, k-early citrus, kiwano, kiwifruit, korean melon, kumquats, lee citrus, lemons, limequat, limes, loganberries, longan, loquat, lychee, mamey sapote, mangoes, mangosteen, mayan melon, melogold, meyer lemon, mombin (jocote), nectarberries, nectarines, olallie berries, olives, orange flesh melon, oranges, oro blanco, ortanique, osceola citrus, page citrus, *papaya*, passion fruit, peaches, pears, pepino, persian melon, persimmons, piel de sapo melon, pineapples, plantains, plums, pomegranates, prunes, pummelo, quenapas, quince, rambutan, raspberries, red currants, royal mandarin, santa claus melon, sapote, satsuma, sharlyn melon, sour orange citrus, spanish melon, sprite melon, strawberries, sweet lime, tamarillo, tangelos, tangerines, tayberries, tejocote (mexican hawthorn), temples, temptation melon, uglifruit/uniqfruit, watermelons, watermelons (seeded), watermelons (seedless), white currants, yellow flesh melon, and the like.

In some instances, plants of the instant disclosure, e.g., that may be treated with the nucleic acids described herein or may be genetically modified to produce the nucleic acids as described herein, are vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (*rappini*), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, *chrysanthemum* leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

Any convenient control element(s) may find use in controlling the expression of the subject nucleic acids in stable and/or transiently transfected plants. In some instances, a subject nucleic acid present in a transgenic plant may be under the control of one or more promoter elements, enhancer elements, repressor elements, etc. Any convenient promoter element, including those described herein, may find use in such transgenic plants, including but not limited to, e.g., constitutive promoters, inducible promoters, tissue specific promoters, and the like. In some instances, a tissue specific promoter may be employed to drive expression in one or more particular plant tissues and/or exclude expression from one or more particular plant tissues. For example, in some instances expression of a subject nucleic acid may be driven in one or more affected tissues (e.g., tissues affected by a plant pest) of the plant and/or one or more tissues or cells of the plant that produce a particular product of the plant. In other instances, expression of a subject nucleic acid may be prevented, e.g., through the use of a tissue specific promoter or repressor, in particular tissues or cell types of the plant, e.g., those tissues or cell types that may be intended for human consumption or used in the production of human or livestock food-stuffs or, e.g., the plant germline.

In some instances, the subject nucleic acids of genetically modified plants may be configured to be inducible, e.g., through the use of inducible promoters or transiently expressed constructs. For example, in some instances, a transgenic plant may be induced to express a subject nucleic acid, as described herein, only when necessary, e.g., during an infestation of a particular pest, during a particular season (e.g., when a particular pest is likely to be present), during a particular stage of the plant lifecycle, etc. In one embodiment, a transgenic plant is induced to express an interfering nucleic acid during an infestation with a pest that feeds on the transgenic plant such that the pest ingests the expressed interfering nucleic acid. Any convenient method of inducing plant transgene expression, e.g., inducing an inducible transgene promoter, inducing a native promoter driving a transgene, etc., may find use in the described methods, including but not limited to the application (e.g., spraying, dusting, watering, etc.) of a liquid, solid, powder, vapor, etc. of or containing an inducing agent or exposure to inducing environmental conditions (e.g., light, temperature, etc.).

In some instances, an expressed interfering nucleic acid is configured such that it does not target the primary organism, e.g., the organism that ingests the expressed nucleic acid from the plant, but instead targets a secondary organism, e.g., an organism that receives the expressed nucleic acid from the primary organism, e.g., through ingestion of the primary organism, consumption of a product produced by the primary organism, through contact with the primary organism, etc. In some instances, the expressed interfering nucleic acid is configured such that it targets the primary organism.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

RNA Extraction, RNA Isolation, and cDNA Synthesis

RNA extractions were performed using either the protocol below or RNeasy® Mini Kits (spin column RNA isolation kit, Qiagen, Hilden, Germany).

RNA was extracted from fresh tissue samples or RNAlater® (RNA stabilization solution, Life Technologies, Grand Island, N.Y.) preserved tissue samples. All tissues were kept on dry ice and remained frozen until homogenized in TRIzol® (RNA extraction solution, Life Technologies, Grand Island, N.Y.). Whole ants were placed into individual tubes containing 1 mL TRIzol® and immediately homogenized with an automatic tissue homogenizer for about 10 seconds or until the tissue was well dispersed, then samples were placed on ice.

Homogenized samples were processed immediately or stored in TRIzol® at −20 degrees C. (deg. C.). Samples were then incubated for 5 min. at room temperature. Following incubation, 200 µL of chloroform were added to the samples and samples were shaken vigorously and vortexed three times to emulsify the solution. Samples were incubated again at room temperature for 2-3 min. and then centrifuged at 12,000×g for 15 min. at 4 deg. C.

Following centrifugation the aqueous phase (about 400 µL) of each sample was transferred to a clean tube, avoiding organic phase and interphase. 250 µL of isopropanol and 250 µL of high salt precipitation solution were added to the samples and samples were mixed by inverting 10 times. RNA was allowed to precipitate overnight at −20 deg. C.

Following precipitation, samples were centrifuged at 12,000×g for 15 min. at 4 deg. C. and the resulting supernatant was discarded. Samples were washed by adding 1 mL of 75% ethanol and mixing by inversion. Samples were re-centrifuged at 12,000×g for 10 min. at 4 deg. C. and supernatant was again discarded. Samples were centrifuged again shortly to allow the removal of any remaining ethanol. Pellets were allowed to air dry for 5-10 min. or until no liquid was visible. Dried pellets were re-suspended in 30-50 µL of RNase free water by gently pipetting the liquid up and down. Re-suspended samples were placed on ice and subsequently used immediately or frozen at −20 deg. C.

Excess DNA was removed from samples using TURBO™ DNA-free Kit (DNA removal kit, Catalog # AM1907, Life Technologies, Grand Island, N.Y.) following the manufacturer's instructions. Following removal of excess DNA samples were used immediately or stored at −20 deg. C.

DNase was removed and RNA was concentrated with alcohol precipitation performed with the following steps: addition of 0.1 volume of 3M sodium acetate and 3 volumes of 100% ethanol, incubation for 25 min. at −20 deg. C., centrifugation at 13,000 rpm for 10 min. at 4 deg. C., discarding of supernatant, washing with 1 mL of 70% ethanol, centrifugation at 13,000 rpm for 5 min., discarding of supernatant, evaporation of ethanol, resuspension with RNase/DNase free water. Samples were used immediately or stored at −20° C.

First strand cDNA synthesis from total RNA was performed by reverse transcription using the SuperScript® III First-Strand Synthesis System (first-strand cDNA synthesis kit, Catalog #18080-051, Life Technologies, Grand Island, N.Y.) and homemade RNase A. The protocol followed for first-strand synthesis is provided below in Table 2.

TABLE 2

| Step 1 | Mix in a 0.2 mL tube: | |
| --- | --- | --- |
| | 50 uM oligo(dt)$_{20}$ | 1 uL |
| | 10 mM dNTP mix | 1 uL |
| | total RNA | 8 uL |
| Step 2 | Heat 65° C. for 5 mins, then put on ice for 1 min. | |
| Step 3 | Prepare cDNA synthesis mix (in the following order): | |
| | 10X Reaction Buffer | 2 uL |
| | 25 mM MgCl$_2$ | 4 uL |
| | 0.1M DTT | 2 uL |
| | 40 U/uL RNaseOUT | 1 uL |
| | 200 U/uL SuperScript III | 1 uL |
| Step 4 | Add mix to RNA/primer mixture, mix, centrifuge | |
| Step 5 | Heat for: | |
| | 50° C. for 50 mins | |
| | 85° C. for 5 mins | |
| | Place on ice | |
| Step 6 | Add 1 uL RNase H and 1 uL RNase A | |
| Step 7 | Heat 37° C. for 20 mins. | |
| Step 8 | Determine DNA concentration on Nanodrop. Dilute to 100 ng/uL. If concentration is <100 ng/uL, adjust qPCR mix. | | qPCR Analysis qPCR was used to check the expression level of target genes. qPCR was performed using SYBR® Select Master Mix (component mix for real-time PCR reaction, Catalog #4472908, Life Technologies, Grand Island, N.Y.) and the Elongase gene specific primers listed below in Table 3. To each qPCR reaction was added: 10 µL 2× qPCR Master Mix, 2 µL of Primer Mix (containing forward and reverse primers), 2 µL of template DNA, and 6 µL of water. The reactions were sealed and placed in the thermal cycler. Thermal cycler programs were varied as necessary. Samples were performed in triplicate and runs included triplicate control reactions using control genes (GAPDH, 18S, ITS, beta Actin, 28S, myosin, etc.). Negative controls (e.g., no template or no primers) and pooled samples were also included in each run and also performed in triplicate. Controls were kept the same between runs to allow direct comparison of results from different runs.

TABLE 3

| qPCRprimers | Primer Name | Primer Sequence | SEQ ID NO: |
| --- | --- | --- | --- |
| LH16891 | LH16891_QPCR_F | ATGCGGTCATGTTCCTTTTC | 32 |
| | LH16891_QPCR_R | TTGTCCTTCGAGTGATGCTG | 33 |
| LH23306 | LH23306_QPCR_F | TGCTTGGACAGAACAAGTCG | 34 |
| | LH23306_QPCR_R | CCAACCGGCAGCTATATGTT | 35 |
| LH17398 | LH17398_QPCR_F | GGCGTCATCAACTCCTTCAT | 36 |
| | LH17398_QPCR_R | ATGGTGGTCAGGTGCTTCTT | 37 |
| LH11439b | LH11439_qPCRF | ATTCAGTTCACGACCGCTTT | 38 |
| | LH11439_qPCRR | CCTTGGCCTTTATCCTCTCC | 39 |
| LH18968 | LH18968_QPCR_F | ACCACATCCAACTTCGCCTA | 40 |
| | LH18968_QPCR_R | ACGTGCAAACTGGAAACCTG | 41 |

Generation of RNAi Constructs and dsRNA Feeding

RNA extraction, isolation, and cDNA synthesis was performed as described above. PCR conditions were optimized for Elongase gene specific primers lacking T7 RNA polymerase binding sites. Following PCR optimization, PCR was performed using primers with flanking T7 polymerase binding sites (i.e. forward and reverse primers with T7 binding sites added to the 5' end of each primer). The T7 containing Elongase primers used in this study are presented in Table 1 which is provided in FIG. 1. 30 μL PCR reactions were performed and two reactions were performed for each gene to get 10 μL of construct. Following PCR, PCR clean-up was performed using QIAquick® PCR Purification Kit (spin column PCR purification kit, Catalog #28106, Qiagen, Hilden, Germany) according to manufacturer's instructions. Following PCR clean-up, PCR products were concentrated and resuspended in 13 μL of nuclease free water.

In vitro transcription was used to generate dsRNA for RNAi feeding. RNA was T7 Flash synthesized using the AmpliScribe™ T7-Flash™ Transcription Kit (Catalog # ASF3507, Epicentre, Madison, Wis.) according to the following protocol provided in Table 4: The RNA transcription reaction generally produced about 10 μL of dsRNA which is enough for about 2 feedings.

TABLE 4

| Step 1 | Mix per tube in the following order in 0.2 mL tube: | |
|---|---|---|
| | Purified DNA | 12.6 uL |
| | 10X Reaction Buffer | 4.0 uL |
| | ATP | 3.6 uL |
| | CTP | 3.6 uL |
| | GTP | 3.6 uL |
| | UTP | 3.6 uL |
| | DTT | 4.0 uL |
| | RNase inhibitor | 1.0 uL |
| Step 2 | Incubate 42° C. for 120 mins | |
| Step 3 | Add 1 uL DNAse I | |
| Step 4 | Incubate 37° C. for 15 mins | |
| Step 5 | Add 20 uL 5M NH₄OAc | |
| Step 6 | Incubate on ice ~15 mins | |
| Step 7 | Centrifuge 10 mins @ 10k rpm | |
| Step 8 | Add 1 mL 70% EtOH, mix well | |
| Step 9 | Centrifuge 15 mins @ 10k rpm, discard supernatant | |
| Step 10 | Evaporate using vacuum centrifuge | |
| Step 11 | Re-suspend in 11.5 uL RNase-free H2O | |
| Step 12 | Determine concentration on Nanodrop, dsRNA should be ~5000 ng/ul | |

Following the production of dsRNA by in vitro transcription, RNAi food was prepared by mixing 5 μL of the concentrated dsRNA with 5 μL of 20% sucrose. Once mixed with sucrose the dsRNA containing RNAi food was fed directly to subject ants.

Analysis of RNAi Mediated Knockdown of Elongase Genes

Ants were fed dsRNA laden food prepared as described above. Ants were fed either control dsRNA targeting GFP or dsRNA targeting an Elongase gene. Following RNAi feeding qPCR was performed at 4 hours, 24 hours, and 48 hours post-feeding to determine the expression level of each targeted gene (LH17389, LH16891, LH23306, LH11439B, and LH18968). The results of the qPCR assay are provided in FIGS. 4-8. Efficient knockdown was seen at at least one time point for Elongase genes LH17389, LH16891, LH23306, and LH18968.

Figure 3:
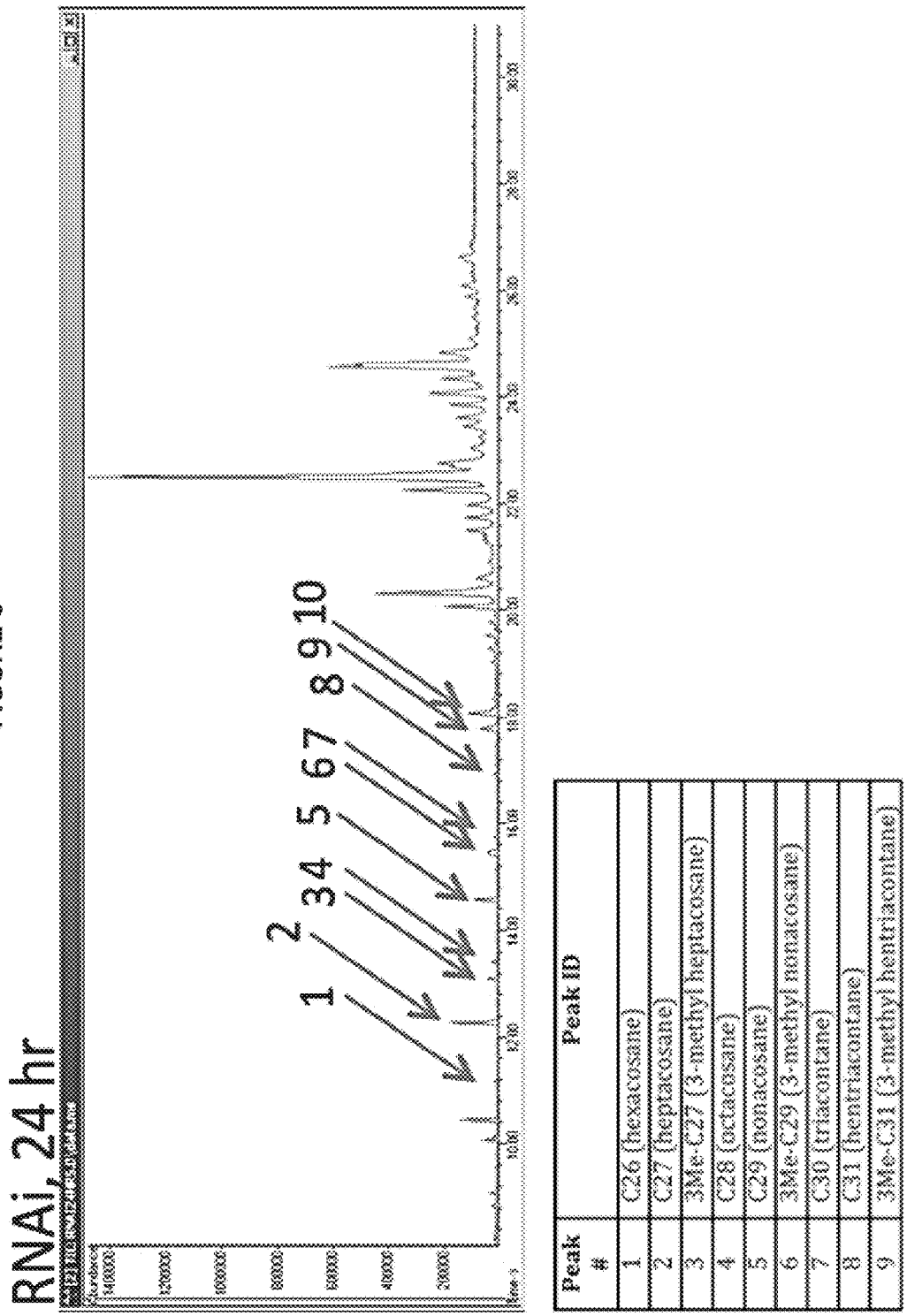
FIG. 3 depicts chemicals present in ants following Elongase RNAi feeding as detected by gas-chromatography-mass spectrometry.
Figure 4:
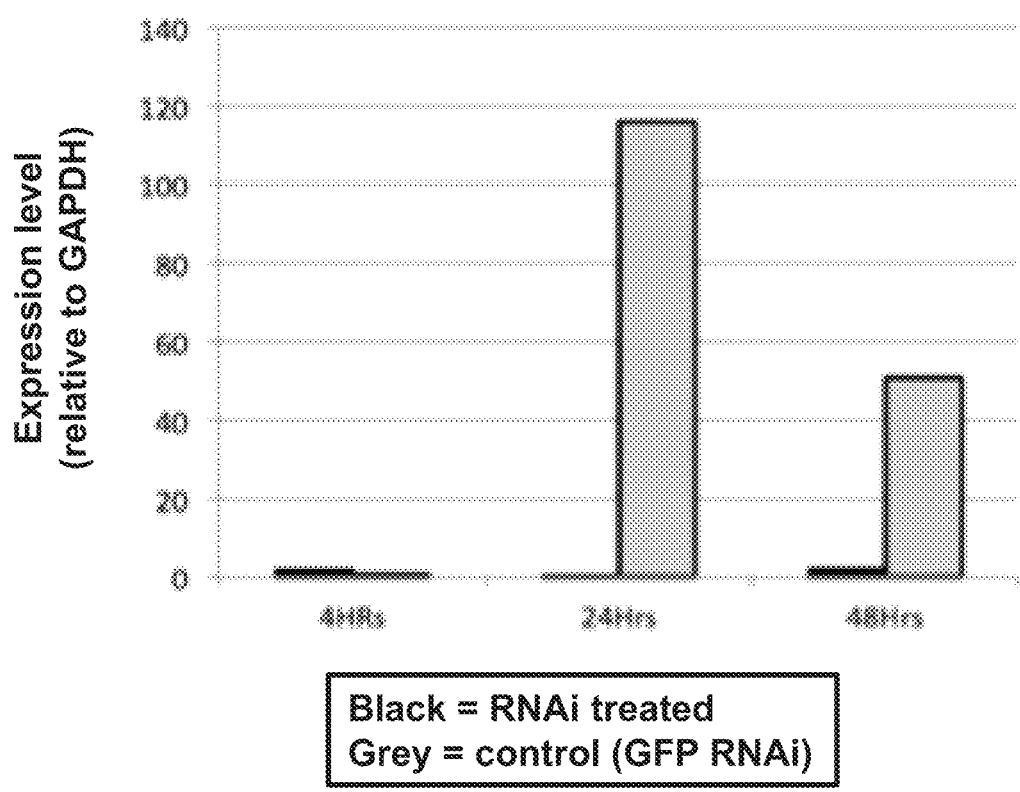
FIG. 4 depicts gene expression levels of Elongase LH17398 following Elongase RNAi feeding as compared to control RNAi feeding.
Figure 5:
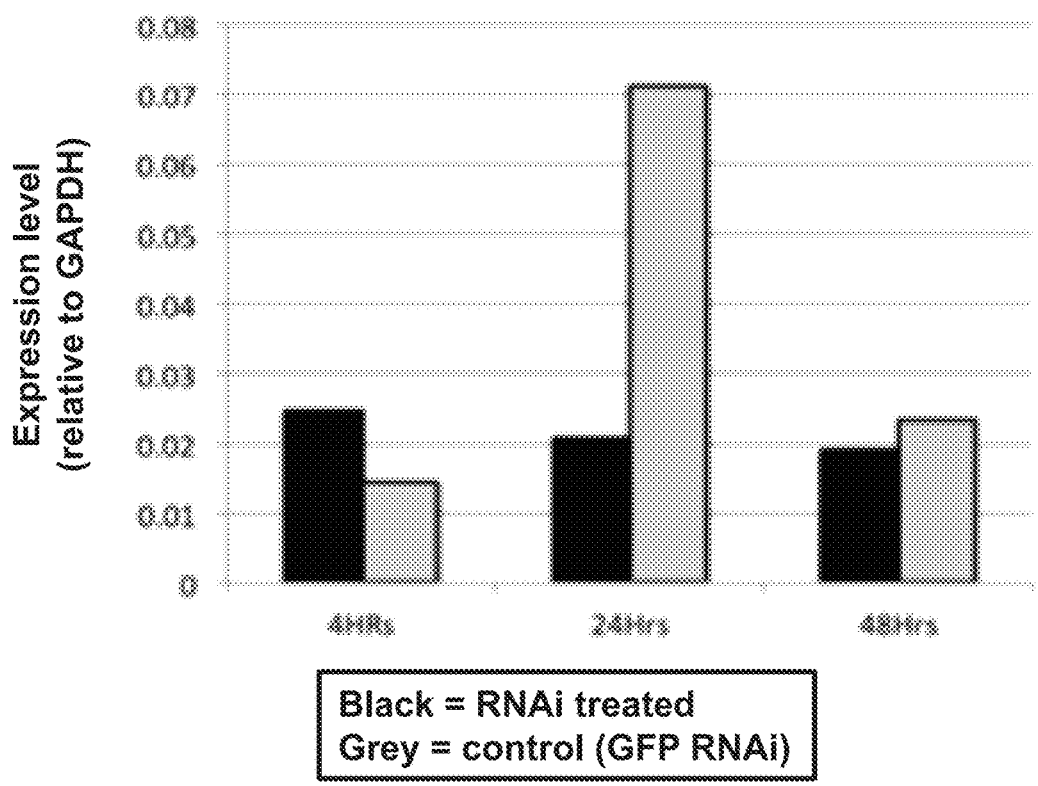
FIG. 5 depicts gene expression levels of Elongase LH16891 following Elongase RNAi feeding as compared to control RNAi feeding.
Figure 6:
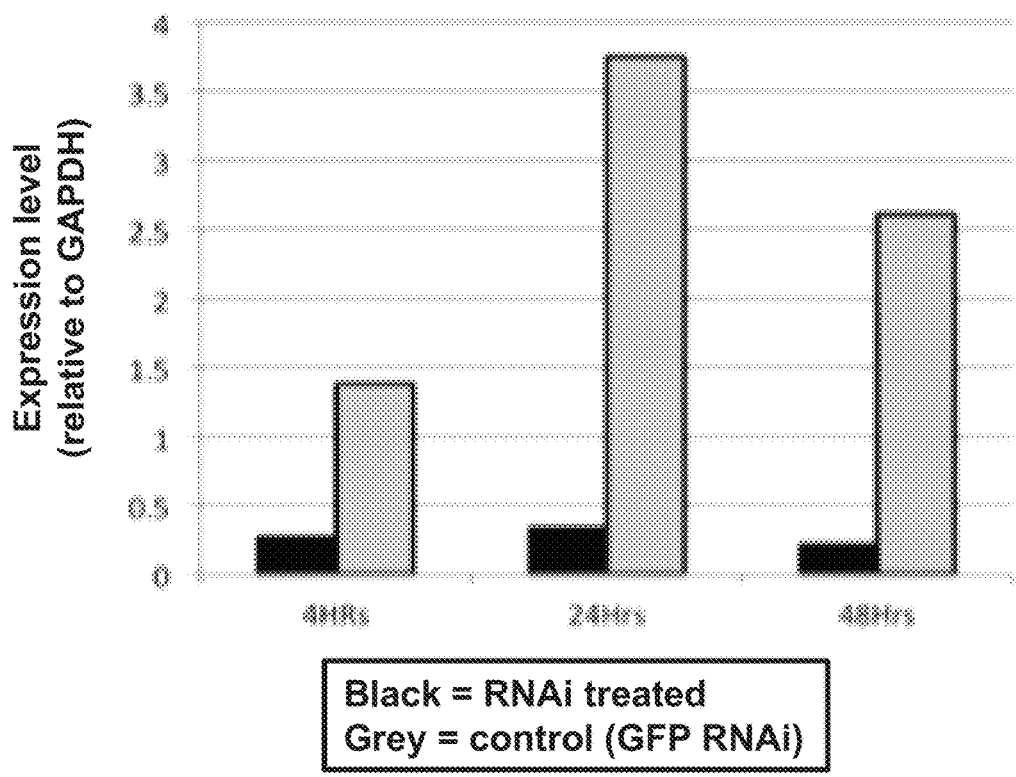
FIG. 6 depicts gene expression levels of Elongase LH23306 following Elongase RNAi feeding as compared to control RNAi feeding.
Figure 7:
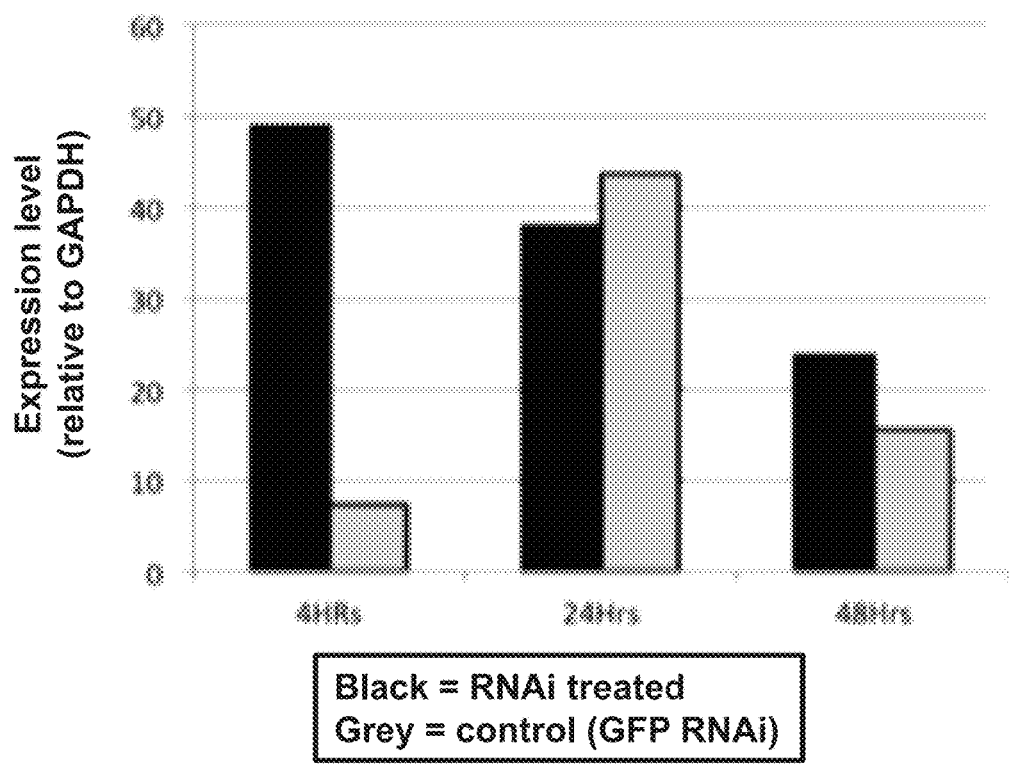
FIG. 7 depicts gene expression levels of Elongase LH11439B following Elongase RNAi feeding as compared to control RNAi feeding.
Figure 8:
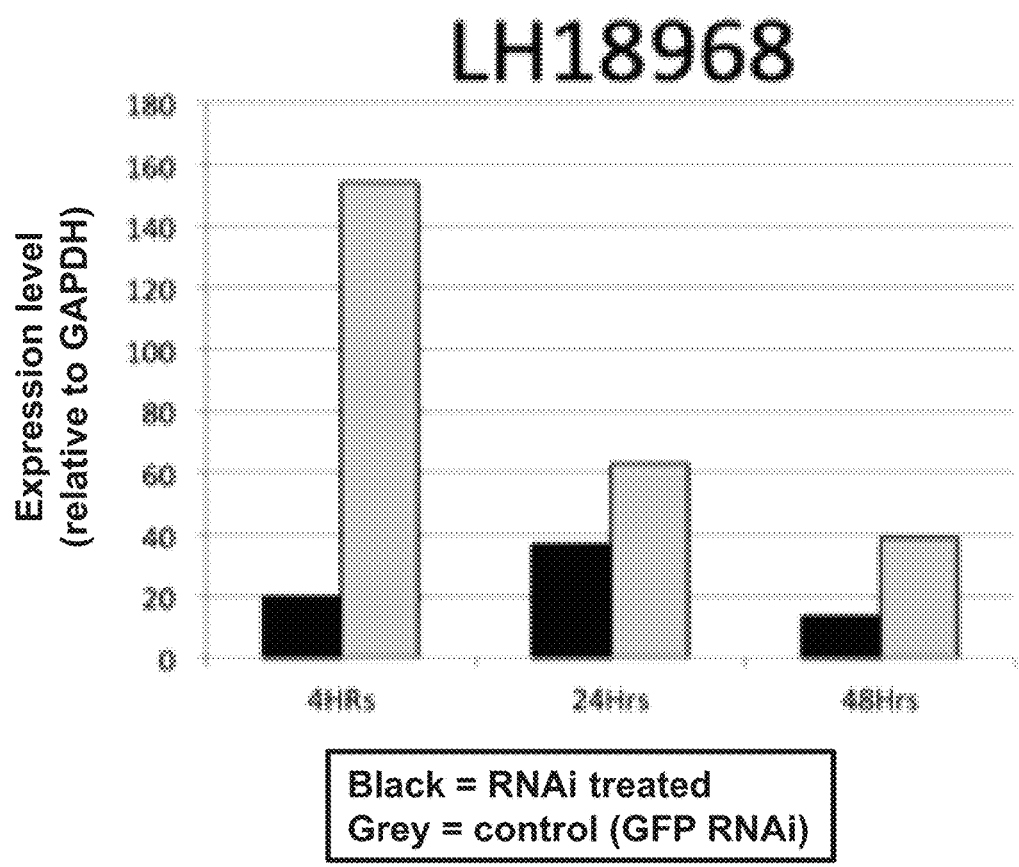
FIG. 8 depicts gene expression levels of Elongase LH18968 following Elongase RNAi feeding as compared to control RNAi feeding.

Following expression analysis, assays were performed to determine if RNAi knockdown of Elongase genes had an effect on ant pheromone production. The chemicals present on the exoskeletons of control ants (i.e. ants fed dsRNA targeting GFP) and Elongase RNAi ants (i.e. ants fed dsRNA targeting Elongase genes) were determined using gas-chromatography-mass spectrometry (GC-MS). The results of the GC-MS analysis are provided in FIGS. 2-3. At least 10 pheromones were reduced or absent in the Elongase RNAi treated ants as compared to the control ants and nine of the chemicals have been identified (C26 (hexacosane), C27 (heptacosane), 3Me-C27 (3-methyl heptacosane), C28 (octacosane), C29 (nonacosane), 3Me-C29 (3-methyl nonacosane), C30 (triacotane), C31 (hentriacontane) and 3Me-C31 (3-methyl hentriacontane)).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A double-stranded RNA that specifically inhibits transcription or translation of an elongase gene involved in cuticular hydrocarbon synthesis in a Hymenoptera host, wherein the elongase gene comprises SEQ ID NO: 13, SEQ ID NO: 14 or SEQ ID NO: 15.

2. A recombinant expression vector comprising heterologous nucleotide sequences encoding a double-stranded RNA that specifically inhibits transcription or translation of an elongase gene involved in cuticular hydrocarbon synthesis in a Hymenoptera host, wherein the elongase gene comprises SEQ ID NO: 13, SEQ ID NO: 14 or SEQ ID NO: 15.

3. A bacterial host cell comprising the interfering nucleic acid of claim 1.

4. A plant genetically modified to express the interfering nucleic acid of claim 1.

5. A composition comprising the interfering nucleic acid of claim 1.

6. The composition according to claim 5, wherein the composition is a spray.

7. The composition according to claim 5, wherein the composition is a liquid.

8. The composition according to claim 5, wherein the composition is a solid or semi-solid.

9. The composition according to claim 5, wherein the composition is a food source for a Hymenoptera host.

10. The composition according to claim 9, wherein the food source is nectar.

11. The composition according to claim 9, wherein the composition comprises an attractant.

12. The composition according to claim 9, wherein the composition comprises a phagostimulant.

13. A method of reducing viability and/or activity of an ant, the method comprising introducing into the ant an effective amount of the double-stranded RNA of claim 1.

14. The method according to claim 13, wherein the double-stranded RNA is effective to reduce one or more of nestmate recognition, queen recognition, larvae recognition, egg recognition, desiccation resistance, and microbial resistance.

15. The recombinant expression vector of claim 2, wherein the nucleotide sequences are operably linked to a promoter.

16. The recombinant expression vector of claim 15, wherein the promoter is an inducible promoter.

17. The double-stranded RNA of claim 1, comprising one or more of a base modification, a sugar modification, and a backbone modification.

18. The double-stranded RNA of claim 1, wherein the double-stranded RNA is produced by transcription of a construct comprising an elongase target sequence, wherein the construct is produced by polymerase chain reaction (PCR) amplification of the elongase target sequence using a set of elongase primers selected from the group consisting:

a) a forward primer comprising the sequence of SEQ ID NO: 1 and a reverse primer comprising the sequence of SEQ ID NO:2; a forward primer comprising the sequence of SEQ ID NO:9 and a reverse primer comprising the sequence of SEQ ID NO: 10;

b) a forward primer comprising the sequence of SEQ ID NO:3 and a reverse primer comprising the sequence of SEQ ID NO:4; and c) a forward primer comprising the sequence of SEQ ID NO:5 and a reverse primer.

* * * * *

UNITED STATES PATENT AND TRADEMARK OFFICE
CERTIFICATE OF CORRECTION

PATENT NO. : 10,450,583 B2
APPLICATION NO. : 15/303173
DATED : October 22, 2019
INVENTOR(S) : Neil D. Tsutsui et al.

Page 1 of 1

It is certified that error appears in the above-identified patent and that said Letters Patent is hereby corrected as shown below:

In the Specification

In Column 1, Line 36, change:
"vester ant (Pogonomyrmex califomicus) populations in"
To:
-- vester ant (Pogonomyrmex californicus) populations in --

In the Claims

In Column 52, Line 64, Claim 18 change:
"NO:5 and a reverse primer."
To:
-- NO:5 and a reverse primer comprising the sequence of SEQ ID NO:6. --

Signed and Sealed this
Twenty-eighth Day of June, 2022

Katherine Kelly Vidal
*Director of the United States Patent and Trademark Office*